(12) United States Patent
Kazumura et al.

(10) Patent No.: US 9,759,639 B2
(45) Date of Patent: Sep. 12, 2017

(54) METHOD FOR PREPARATION OF ALGAL CELLS, AND KIT FOR EVALUATION OF TOXICITY OF CHEMICAL SUBSTANCE

(75) Inventors: Kimiko Kazumura, Hamamatsu (JP); Ayano Takeuchi, Hamamatsu (JP); Masakazu Katsumata, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 19 days.

(21) Appl. No.: 13/821,326

(22) PCT Filed: Jul. 14, 2011

(86) PCT No.: PCT/JP2011/066150
§ 371 (c)(1),
(2), (4) Date: Mar. 28, 2013

(87) PCT Pub. No.: WO2012/032853
PCT Pub. Date: Mar. 15, 2012

(65) Prior Publication Data
US 2013/0177967 A1    Jul. 11, 2013

(30) Foreign Application Priority Data
Sep. 8, 2010 (JP) ................. 2010-201142

(51) Int. Cl.
G01N 1/30 (2006.01)
C12N 1/04 (2006.01)
C12N 1/12 (2006.01)
C12Q 1/02 (2006.01)

(52) U.S. Cl.
CPC ........... *G01N 1/30* (2013.01); *C12N 1/04* (2013.01); *C12N 1/12* (2013.01); *C12Q 1/025* (2013.01); *G01N 2333/405* (2013.01)

(58) Field of Classification Search
None
See application file for complete search history.

(56) References Cited

U.S. PATENT DOCUMENTS

2007/0224659 A1    9/2007    Katsumata et al.

FOREIGN PATENT DOCUMENTS

| CN | 1898552 | 1/2007 |
|---|---|---|
| WO | WO-2005/062027 | 7/2005 |
| WO | WO-2007/097341 | 8/2007 |
| WO | WO-2011/055658 | 5/2011 |

OTHER PUBLICATIONS

Araujo, Cristiano VM; et al; "Effects of cold-dark storage on growth of Cylindrotheca closterium and its sensitivity to copper" Chemosphere, 72, 1366-1372, 2008.*

Kuzmina, Julie; "Progress Report on Cryopreservation at the University of Toronto Culture Collection of Algae and Cyanobacteria" University of Toroonto, Progress Report, 2004.*

Day, J.G., et al., "Cryopreservation of Algae", Methods in Molecular Biology, vol. 38, Cryopreservation and Freeze Drying Protocols, 1995, p. 81-p. 89.

Katsumata M., et al., "Rapid ecotoxicological bioassay using delayed fluorescence in the green alga *Pseudokirchneriella subcapitata*", Water research, 2006, vol. 40, p. 3393-3400.

Masakazu Katsumata et al., "Application of Delayed Luminescence for Algal Bioassay: Determination of Influences of Chemical Substance on Alga", Kankyo Kenkyu, vol. 139, 2005, pp. 107 to 112.

Kazuyoshi Kuwano, "Sorui no Toketsu Hozon, 21 Seiki Shoto no Sogaku no Genkyo", 2002, pp. 108-111.

Fumi Mori et al., "Cryopreservation of Cyanobacteria and Green Algae in the NIES-Collection", Microbiol. Cult. Coll, 2002, vol. 18, No. 1, pp. 45 to 55.

Fumi Mori, "Cryopreservation methods of microalgae", Microbiol. Cult., Coll., 2007, vol. 23, No. 2, pp. 89 to 93.

Romo S., et al., "Preservation of filamentous cyanobacteria cultures (Pseudanabaena galeata) Bocher and Geitlerinema amphibium (Ag. ex Gom.) Anagn. under low temperatures", Journal of microbiological methods, 1992, vol. 16, p. 85-89.

Katsumata M., et al., "New feature of delayed luminescence: Preillumination-induced concavity and convexity in delayed luminescence decay curve in the green alga *Pseudokirchneriella subcapitata*", Journal of Photochemistry and Photobiology B: Biology, vol. 90, Iss. 3, 2008, p. 152-162.

Masakazu Katsumata et al., "Influences of Herbicides and Mercury on Blue-Green Alga *Spirulina platensis*—Analysis of Long-Term Behavior of *S. platensis* Delayed Fluorescence", Journal of Japan Society on Water Environment, vol. 28, No. 1, 2005, pp. 23 to 28.

Masakazu Katsumata et al., "Shokubutsu no Bijaku Hakko Keisoku Gijutsu", Optical alliance, Jun. 2010, vol. 21, No. 6, pp. 28 to 33.

Masakazu Katsumata et al., "Shokubutsu Bijaku Hakko Keisoku Gijutsu to sono Sorui Bioassay ene Oyo", Optical and Electro-optical Engineering Contact, 2009, vol. 47, No. 7, pp. 368-375.

Masakazu Katsumata et al., "Sorui ni Taisuru Kagaku Busshitsu no Dokusei Hyoka eno Chlorophyll Chien Hakko no Riyo Kanosei", Dai 45 Kai Japan Society on Water Environment Nenkai Koenshu, Mar. 18, 2011 (Mar. 18, 2011), p. 97, 1-H-11-4.

Ayano Takeuchi et al, "Chlorophyll Chien Hakko o Riyo shita Sorui ni Taisuru Kagaku Busshitsu no Dokusei no Jinsoku Hyokaho", Dai 45 Kai Japan Society on Water Environment Nenkai Koenshu, Mar. 18, 2011 (Mar. 18, 2011), p. 695, P-No4.

Malik et al., "Preservation of unicellular green algae by a liquid-drying method", Journal of Microbiological Methods, Elsevier, Amsterdam, NL, vol. 18, No. 1, [retrieved on Jul. 1, 1993], Jul. 1, 1993, pp. 41 to 49, XP023699431.

Schumann et al., "Chlorophyll extraction methods for the quantification of green microalgae colonizing building facades", International Biodeterioration and Biodegradation, Elsevier Ltd, GB, vol. 55, No. 3, [retrieved on Apr. 1, 2005], Apr. 1, 2005, pp. 213 to 222, XP027868498.

(Continued)

*Primary Examiner* — David Berke-Schlessel
(74) *Attorney, Agent, or Firm* — Drinker Biddle & Reath LLP

(57) ABSTRACT

The present invention provides a method for preparing algal cells used for evaluating a toxicity of a chemical substance by delayed luminescence, the method comprising the step of freezing algal cells in a logarithmic growth phase.

5 Claims, 26 Drawing Sheets

(56) References Cited

OTHER PUBLICATIONS

Ben-Amotz et al., "Cryopreservation of Marine Unicellular Algae. I. A. Survey of Algae with Regard to Size, Culture, Age, Photosynthetic Activity and Chlorophyll-to-Cell Ratio", Marine Ecology Progress Series, vol. 2, Jan. 1, 1980, pp. 157 to 161, XP055096950.
Pedro Caňavate et al., "Effects of culture age on cryopreservation of marine microalgae", European Journal of Phycology, vol. 32, No. 1, Feb. 1, 1997, pp. 87 to 90, XP055096951.
Taylor et al., "Cryopreservation of eukaryotic algae—a review of methodologies", Journal of Applied Phycology, vol. 10, No. 5, Jan. 1, 1998, pp. 481 to 501, XP055096953.
Au Benhra et al., "Cryoalgotox: Use of Cryopreserved Alga in a Semistatic Microplate Test", Environmental Toxicology and Chemistry, vol. 16, No. 3, 1997, p. 505-p. 508.

\* cited by examiner

METHOD FOR PREPARATION OF ALGAL CELLS, AND KIT FOR EVALUATION OF TOXICITY OF CHEMICAL SUBSTANCE

TECHNICAL FIELD

The present invention relates to a method for preparing algal cells and a kit for evaluating a toxicity of a chemical substance.

BACKGROUND ART

For evaluating a toxicity of a chemical substance using algae, it is necessary to prepare algal cells by performing primary and passage cultures based on cells maintained in a liquid culture, an agar medium, or the like, add the test substance to the prepared algal cells, and conduct a test. However, it is cumbersome and inconvenient to maintain algal cells and perform a passage culture for each test.

For eliminating this cumbersomeness, frozen algal cells (Non Patent Literatures 1 and 2, etc.) can be utilized. Thawing frozen algal cells immediately before a test and using the thawed algal cells can rapidly subject the algal cells to a test without passage cultures.

CITATION LIST

Patent Literature

Patent Literature 1: International Publication No. 2005/062027

Non Patent Literature

Non Patent Literature 1: KUWANO Kazuyoshi, "Cryopreservation of Algae," HORI Terumitsu, OHNO Masao, and HORIGUCHI Takeo, ed., *State of Phycology in the Early 21st Century*, Japanese Society of Phycology, Yamagata, p. 108-111.

Non Patent Literature 2: MORI Fumi et al., "Cryopreservation of Cyanobacteria and Green Algae in the NIES-Collection," *Microbiol. Cult. Coll.*, June 2002, p. 45-55.

Non Patent Literature 3: J. G. Day et al., "Cryopreservation of Algae", *Methods in Molecular Biology*, Vol. 38, Cryopreservation and Freeze Drying Protocols, p. 81-89

SUMMARY OF INVENTION

Technical Problem

As the algal cells to be frozen, cells in a stationary phase are typically used. This is because the time for thawing them into viable cells can be reduced thereby, while intracellular substances such as lipids act as cytoprotectants (Non Patent Literature 3).

In methods for evaluating toxicities of chemical substances using algae, the inventors have already developed a method utilizing delayed luminescence of algae (Patent Literature 1) as a method easier than the growth inhibition test defined in the test guideline TG201 of Organisation for Economic Co-operation and Development (OECD). However, the inventors have found that freezing, thawing, and cultivating algal cells in the stationary phase makes them grow worse than unfrozen cells. Since the growth of cells affects the toxicity evaluation by delayed luminescence, using the stationary-phase algal cells incurs a problem that the toxicity evaluation on a par with the one using unfrozen algal cells cannot be performed. It is therefore necessary to prepare frozen cells of algae which grow well after thawing.

Solution to Problem

For achieving the above-mentioned object, the inventors conducted diligent studies and have found that using cells in a logarithmic growth phase as algal cells to be frozen makes thawed algal cells grow smoothly, thereby accomplishing the present invention.

That is, the present invention provides a method for preparing algal cells used for evaluating a toxicity of a chemical substance by delayed luminescence, the method comprising the step of freezing algal cells in a logarithmic growth phase. Freezing the cells in the logarithmic growth phase makes thawed algal cells grow favorably, while allowing delayed luminescence to yield a light emission quantity as strong as that before freezing.

Preferably at least 50% of the total number of the algal cells to be frozen have a particle size of 4.5 µm or greater. Preferably, the algal cells to be frozen exhibit a bimodal particle size distribution curve. Using such algal cells allows thawed algal cells to grow more favorably and makes it easier for the delayed luminescence to yield a light emission quantity as strong as that before freezing.

Preferably, when using green algae (Pseudokirchneriella subcapitata) preserved as strain No. NIES-35 in National Institute for Environmental Studies as the algal cells to be frozen, at least 55% of the total number of the algal cells to be frozen have a particle size not smaller than that at a valley value in the bimodal particle size distribution curve. Also, when using the green algae preserved as strain No. NIES-35 in National Institute for Environmental Studies, the number of cells at the larger-particle-size peak in the bimodal particle size distribution curve is preferably at least 50% of the total of the number of cells at the smaller-particle-size peak and the number of the cells at the larger-particle-size peak. When the green algae preserved as strain No. NIES-35 are used, employing the algal cells having the above-mentioned particle size distribution allows the thawed algal cells to grow more favorably.

Preferably, when using green algae (Pseudokirchneriella subcapitata) preserved as ATCC No. 22662 in the American Type Culture Collection as the algal cells to be frozen, at least 46% of the total number of the algal cells to be frozen have a particle size not smaller than that at a valley value in the bimodal particle size distribution curve. Also, when using the green algae preserved as ATCC No. 22662 in the American Type Culture Collection, the number of cells at the larger-particle-size peak in the bimodal particle size distribution curve is preferably at least 37% of the total of the number of cells at the smaller-particle-size peak and the number of the cells at the larger-particle-size peak. When the green algae preserved as ATCC No. 22662 are used, employing the algal cells having the above-mentioned particle size distribution allows the thawed algal cells to grow more favorably.

Preferably the method of the present invention further comprises, before the step of freezing the algal cells in the logarithmic growth phase, the steps of cultivating the algal cells in the logarithmic growth phase in a culture solution, centrifuging the culture solution containing the algal cells, and completely removing from the algal cells a culture supernatant separated by the centrifuging. Completely removing the culture supernatant from the algal cells reduces the influence of the freezing and thawing on a delayed luminescence pattern, thereby making it easier to yield a delayed luminescence pattern on a par with that of the unfrozen cells.

Preferably the method of the present invention further comprises the step of maintaining the frozen algal cells in the logarithmic growth phase at a temperature of −80° C. or below. Maintaining them at a temperature of −80° C. or below can prevent the cells from being damaged during freezing, whereby the thawed algal cells grow more favorably.

The present invention also provides a kit for evaluating a toxicity of a chemical substance by delayed luminescence, the kit including frozen cells in a logarithmic growth phase. Using such a kit can evaluate the toxicity of the chemical substance easily and rapidly by delayed luminescence.

Preferably at least 50% of the total number of the frozen algal cells have a particle size of 4.5 μm or greater, and the algal cells preferably exhibit a bimodal particle size distribution curve.

Preferably, while the frozen algal cells included in the toxicity evaluation kit are green algae (Pseudokirchneriella subcapitata) preserved as strain No. NIES-35 in National Institute for Environmental Studies, at least 55% of the total number of the frozen algal cells have a particle size not smaller than that at a valley value in the bimodal particle size distribution curve, and the number of cells at the larger-particle-size peak in the bimodal particle size distribution curve is preferably at least 50% of the total of the number of cells at the smaller-particle-size peak and the number of cells at the larger-particle-size peak.

Preferably, while the frozen algal cells included in the toxicity evaluation kit are green algae (Pseudokirchneriella subcapitata) preserved as ATCC No. 22662 in the American Type Culture Collection, at least 46% of the total number of algal cells to be frozen have a particle size not smaller than that at a valley value in the bimodal particle size distribution curve, and the number of cells at the larger-particle-size peak in the bimodal particle size distribution curve is preferably at least 37% of the total of the number of cells at the smaller-particle-size peak and the number of the cells at the larger-particle-size peak.

The frozen algal cells included in the toxicity evaluation kit are preferably prepared by a method comprising the steps of cultivating the algal cells in the logarithmic growth phase in a culture solution, centrifuging the culture solution containing the algal cells, completely removing from the algal cells a culture supernatant separated by the centrifuging, and freezing the remaining algal cells.

Preferably the algal cells included in the toxicity evaluation kit are maintained at a temperature of −80° C. or below.

Advantageous Effects of Invention

The method for preparing algal cells in accordance with the present invention allows the frozen and thawed algal cells to grow favorably, so that they can be used for toxicity evaluation of the chemical substance by delayed luminescence as with the unfrozen algal cells. The kit for evaluating a toxicity of a chemical substance by delayed luminescence in accordance with the present invention can evaluate the toxicity of the chemical substance easily and rapidly.

DESCRIPTION OF EMBODIMENTS

Figure 1:
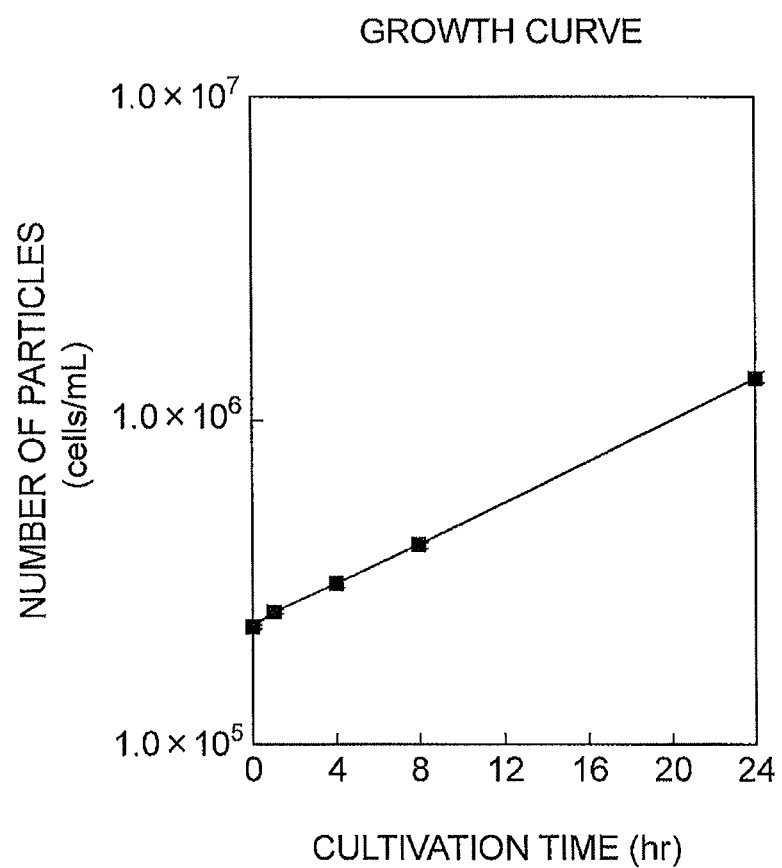
FIG. 1 is a graph illustrating a growth curve of the thawed green algae cells frozen in the logarithmic growth phase (Example 1)

In the following, modes for carrying out the present invention will be explained in detail with reference to the attached drawings as appropriate.

The preparation method of the present invention includes freezing algal cells in a logarithmic growth phase. More specifically, it cultivates the algal cells to the logarithmic growth phase, collects the cultivated algal cells, and freezes and preserves the collected algal cells. The freeze-preserved algal cells are thawed and used for evaluating a toxicity of a chemical substance by delayed luminescence.

By "logarithmic growth phase" in this specification is meant a period in which the algal cells multiply by separating into two for each fixed time, so that the number of cells grows logarithmically with time. By "stationary phase" is meant a period in which the division rate and death rate substantially reach equilibrium, whereby the number of cells becomes nearly constant.

As algal cells usable in the present invention, algal cells such as green algae (*Pseudokirchneriella subcapitata* (formerly known as *Selenastrum capricornutum*) and *Desmodesmus subspicatus* (formerly known as *Scenedesmus subspicatus*)), blue-green algae (*Anabaena flos-aquae* and *Synechococcus leopoliensis*), and diatoms (*Navicula pelliculosa*) may be used. As green algae (*Pseudokirchneriella subcapitata*), for example, those preserved as strain No. NIES-35 in National Institute for Environmental Studies (hereinafter referred to as "NIES-35 strain" as the case may be) and those preserved as ATCC No. 22662 in the American Type Culture Collection (hereinafter referred to as "ATCC-22662 strain" as the case may be) may be used. The strains preserved in these organizations are preferred in that they are stable with less variability in property among individuals.

Standard methods can be used for cultivating the algal cells to the logarithmic growth phase. When green algae (*Pseudokirchneriella subcapitata*) are employed as the algal cells, for example, preparing cells in the stationary phase at an initial cell density of $1 \times 10^4$ cells/mL and cultivating them for 70 to 73 hr by using a culture solution such as a C(75) medium or an OECD medium under a condition with a temperature of 25±0.5° C. and an illuminance of 50 to 55 $\mu mol \cdot m^{-2} \cdot s^{-1}$ can yield the cells in the logarithmic growth phase. The fact that they are the cells in the logarithmic growth phase can be seen by counting the number of obtained cells three or more times within a fixed period with a particle counter (CDA-500), logarithmically plotting the number of cells with cultivation time, and finding that thus produced growth curve is substantially linear.

Among the cultivated algal cells in the logarithmic growth phase, a cell group preferred as the one used for the method of the present invention can be determined with reference to the particle size of cells as an index. Preferably, cells having a large particle size are frozen in the method of the present invention. Specifically, when the number of algal cells to be frozen is assumed to be 100%, i.e., with respect to the total number of algal cells to be frozen, the number of algal cells having a particle size of 4.5 µm or greater is preferably at least 50%, more preferably at least 53%, further preferably at least 57%. By "particle size" of algal cells in the specification is meant the diameter of algal cells computed by a particle size distribution analyzer of an electrical sensing zone type. Preferably, the algal cells to be frozen exhibit a bimodal particle size distribution curve. The bimodal distribution indicates a two-phase distribution exhibiting two large peaks. Such cells preferable for freezing can be seen from data obtained by counting the number of cells.

Using the algal cells having a bimodal particle size distribution as such seems to have the following significance. The state of cells at the time of freezing greatly affects the cell growth after thawing. In order for the cells thawed from the freeze-preserved state to grow logarithmically with rapidity, the cells to be frozen are preferably in a state separated into two groups composed of a group of larger cells before cell division and a group of smaller cells immediately after the cell division. The separation into two groups indicates a state where the cell division is actively under way.

A more preferred cell group in the algal cells exhibiting a bimodal particle size distribution can be determined according to the particle size at a valley value as an index. By "particle size at a valley value" in the specification is meant the particle size at which the number of cells becomes the minimum between two peaks in a bimodal particle size distribution curve. The particle size at the valley value is preferably not too large. As the valley value is greater, the smaller-particle-size group occupies a greater ratio, i.e., the cell growth is lower in the cell group. One of reasons therefor is that nutrient salts, light energy, carbon dioxide, and the like which are essential for biomass production become scarcer and depleted as the cells increase. When frozen in a state where the cell growth is lowered, the cells tend to be hard to grow logarithmically immediately after thawing. Therefore, the particle size at the valley value is preferably not too large. Specifically, the particle size at the valley value is preferably about 4 to 5 µm.

When the NIES-35 strain cells are employed as the algal cells, it is also preferred for them to exhibit a bimodal particle size distribution curve. When the number of algal cells to be frozen is assume to be 100%, i.e., with respect to the total number of algal cells to be frozen, the number of algal cells having a particle size not smaller than that at the valley value in the bimodal particle size distribution curve is preferably at least 55%, more preferably at least 76%. When the NIES-35 strain cells are employed as the algal cells, assuming that the total of the number of cells at the smaller-particle-size peak and the number of cells at the larger-particle-size peak in the bimodal particle size distribution curve is 100%, i.e., with respect to the total, the number of cells at the larger-particle-size peak is preferably at least 50%, more preferably at least 72%. By "the cell number at a peak" in the specification is meant the number of cells having a particle size of P±0.02 µm, where P µm is the particle size at the peak. When the NIES-35 strain cells are used, the valley value is preferably less than 4.52 µm, more preferably 4.40 µm or less, further preferably 4.12 µm or less.

When the ATCC-22662 strain cells are employed as the algal cells, it is also preferred for them to exhibit a bimodal particle size distribution curve. When the number of algal cells to be frozen is assumed to be 100%, i.e., with respect to the total number of algal cells to be frozen, the number of algal cells having a particle size not smaller than that at the valley value in the bimodal particle size distribution curve is preferably at least 46%, more preferably at least 48%. When the ATCC-22662 strain cells are employed as the algal cells, assuming that the total of the number of cells at the smaller-particle-size peak and the number of cells at the larger-particle-size peak in the bimodal particle size distribution curve is 100%, i.e., with respect to the total, the number of cells at the larger-particle-size peak is preferably at least 37%, more preferably at least 41%. When the ATCC-22662 strain cells are used, the valley value is preferably less than 4.87 µm, more preferably 4.78 µm or less.

When using either the NIES-35 or ATCC-2266 strain cells as the algal cells, whether or not a cell group is suitable for use in the method of the present invention can be determined by various methods other than those mentioned above.

When the particle size distribution curve is bimodal, for example, separating the cells into two groups composed of "larger cells" having a particle size greater than that at the valley value and "smaller cells" having a particle size smaller than that at the valley value and comparing the integrated value of a predetermined particle size and the number of cells at the predetermined particle size (particle size×cell number) per group (hereinafter referred to as "characteristic amount") between the "larger cells" and "smaller cells" can determine whether or not a cell group is a preferred cell group. By "the number of cells at a predetermined particle size" is meant the number of cells having a particle size of Q±0.02 μm, where Q μm is the predetermined particle size. Assuming that the total of characteristic amounts of the "larger cells" and "smaller cells" is 100%, i.e., with respect to the total, the characteristic amount of the "larger cells" is preferably at least 64% in the case of NIES-35 strain and at least 53% in the case of ATCC-22662 strain.

Similarly, when the particle size distribution curve is bimodal, separating the cells into two groups composed of "larger cells" having a particle size greater than that at the valley value and "smaller cells" having a particle size smaller than that at the valley value and comparing the integrated value of the particle size at a peak and the number of cells at the peak (peak particle size×cell number, hereinafter referred to as "characteristic amount representative value") between the "larger cells" and "smaller cells" can determine whether or not a cell group is a preferred cell group. Assuming that the total of characteristic amounts of the "larger cells" and "smaller cells" is 100%, i.e., with respect to the total, the characteristic amount representative value ratio of the "larger cells" is preferably at least 61% in the case of NIES-35 strain and at least 43% in the case of ATCC-22662 strain.

Whether or not a cell group is suitable for the method of the present invention can also be determined from the surface area or volume of the algal cells for use. When the surface area of algal cells is known, for example, an approximate value of particle size can be calculated by $$\text{Particle size} = 2 \times \sqrt{\frac{\text{surface area}}{4\pi}}, \qquad [\text{Math. 1}]$$

and whether or not a cell group is suitable for use in the method of the present invention can be determined according to the particle size as an index as mentioned above. When the volume of algal cells is known, on the other hand, an approximate value of particle size can be calculated by $$\text{Particle size} = 2 \times \sqrt[3]{\frac{3 \times \text{volume}}{4\pi}}, \qquad [\text{Math. 2}]$$

and whether or not a cell group is suitable for use in the method of the present invention can be determined according to the particle size as an index as mentioned above.

The cultivated cells can be collected by known methods. For example, the cells may be precipitated by centrifuging, so that the precipitated cells can be collected together with the culture solution. For maintaining the cells in the logarithmic growth phase and attaining a delayed luminescence pattern after a recovery cultivation on a par with that of the unfrozen cells, it is preferred that the culture supernatant after the precipitation be removed completely and the remnant be suspended in a new culture solution. For complete removal, it will be sufficient if the culture supernatant is aspirated by an aspirator or the like, so as to be reduced to such an extent that it is visually unrecognizable after the aspiration. If a frost damage protectant is used in a later step, the culture solution will be diluted by the frost damage protectant, whereby the culture solution for suspending the cells can be used by an amount smaller than that of the culture solution for cultivating the cells to the logarithmic growth phase. For example, the cells can be suspended in a new culture solution whose amount is 1/100 that of the culture solution used for cultivating the cells to the logarithmic growth phase. In such a manner, the frost damage protectant content ratio can be made smaller when preparing a control sample or exposure sample for use in a toxicity evaluation of a chemical substance by delayed luminescence after thawing. When no frost damage protectant is used, it is sufficient for the cells cultivated before freezing to be maintained in the logarithmic growth phase, and the cell suspension may directly be used for freezing thereafter.

The frost damage protectant may be added to the cell suspension for freezing. Usable as the frost damage protectant are known frost damage protectants such as DMSO (dimethyl sulfoxide), for example, which can be contained in the culture solution before freezing by a concentration of 5 to 10%, more preferably 5%. The frost damage protectant can be added by preparing the frost damage protectant by an appropriate concentration and mixing it with the cell suspension.

Thus prepared cell suspension is left at room temperature as appropriate and then slowly cooled to freeze by a deep freezer or the like. The cell suspension is put into a cryo tube or the like, which is contained in a freezer container equipped with a protective material, which is wrapped with a shock-absorbing material or the like, so as to be cooled in the deep freezer or the like. The suspension is preferably cooled to a temperature of −80° C. or below preferably at a cooling rate of about 1° C./min. Thus slowly cooling to freeze is preferred in that it can prevent the cells from being damaged in the process of cooling. Preferably, the suspension is cooled to a temperature of −80° C. or below and then maintained as it is at a temperature of −80° C. or below. Maintaining it at a temperature of −80° C. or below can prevent the cells from being damaged during freezing and allow the thawed cells to grow more favorably.

The frozen algal cells can be freeze-preserved as they are for a long period thereafter and thawed when used for evaluating a toxicity of a chemical substance by delayed luminescence. A method which will be explained later, for example, can evaluate the toxicity of the chemical substance using the algal cells prepared by the present invention.

The present invention also provides a kit for evaluating a toxicity of a chemical substance by delayed luminescence. The kit for evaluating a toxicity of a chemical substance by delayed luminescence in accordance with the present invention includes frozen algal cells in the logarithmic growth phase. Preferably the frozen cells in the logarithmic growth phase are the algal cells prepared by the method explained above. Preferably the algal cells are maintained at a temperature of −80° C. or below in the kit. The kit of the present invention may further comprise culture solutions, stabilizers, reagents, cell culture vessels, sample collecting tools, shock-absorbing materials, containers, user manuals, attached documents, and the like as appropriate. Using the kit of the present invention can evaluate the toxicity of the chemical substance by delayed luminescence easily and rapidly.

A method for evaluating a toxicity of a chemical substance by delayed luminescence using the algal cells prepared by the method of the present invention will now be explained.

The present invention provides a method for evaluating a toxicity of a chemical substance using algae, the method comprising:
(a) a thawing step of thawing frozen algal cells by heating and diluting thus obtained cell suspension with a medium;
(b) a recovery cultivation step of cultivating the algal cells obtained by the thawing step (a) so that the algal cells recover from influences of freezing and thawing;
(c) a validation step of taking a part of the algal cells after the recovery cultivation step (b), diluting it with a medium, measuring delayed luminescence of the algal cells, and adopting thus obtained light emission quantity as initial value data;
(d) an exposure step of producing an exposure sample by mixing the algal cells after the validation step (c) and a solution containing a test substance and cultivating the exposure sample;
(e) a measurement step of measuring delayed luminescence of the exposure sample after the exposure step (d) and adopting thus obtained light emission quantity as exposure data; and
(f) an evaluation step of computing an evaluation value according to the initial value data and exposure data and evaluating the toxicity of the test substance according to the evaluation value.

For more accurate evaluation, it is preferable for the above-mentioned method to repeat the recovery cultivation step (b) and validation step (c) until the initial value data obtained by the validation step (c) reaches a predetermined value.

In order for the above-mentioned method to perform more accurate evaluation, it is preferable that the exposure step (d) further produce a control sample by mixing the algal cells after the validation step (c) and a solvent of the test substance solution and cultivate the control sample, the measurement step (e) further measure delayed luminescence of the control sample and adopt it as control data, and the evaluation step (f) compute the evaluation value according to the initial value data, exposure data, and control data and evaluate the toxicity of the test substance according to the evaluation value.

The method for evaluating a toxicity of a chemical substance using algae in accordance with the present invention can yield the same light emission pattern as that of unfrozen algal cells without lowering the light emission quantity, thereby making it possible to evaluate the toxicity rapidly by using frozen algal cells.

Figure 26:
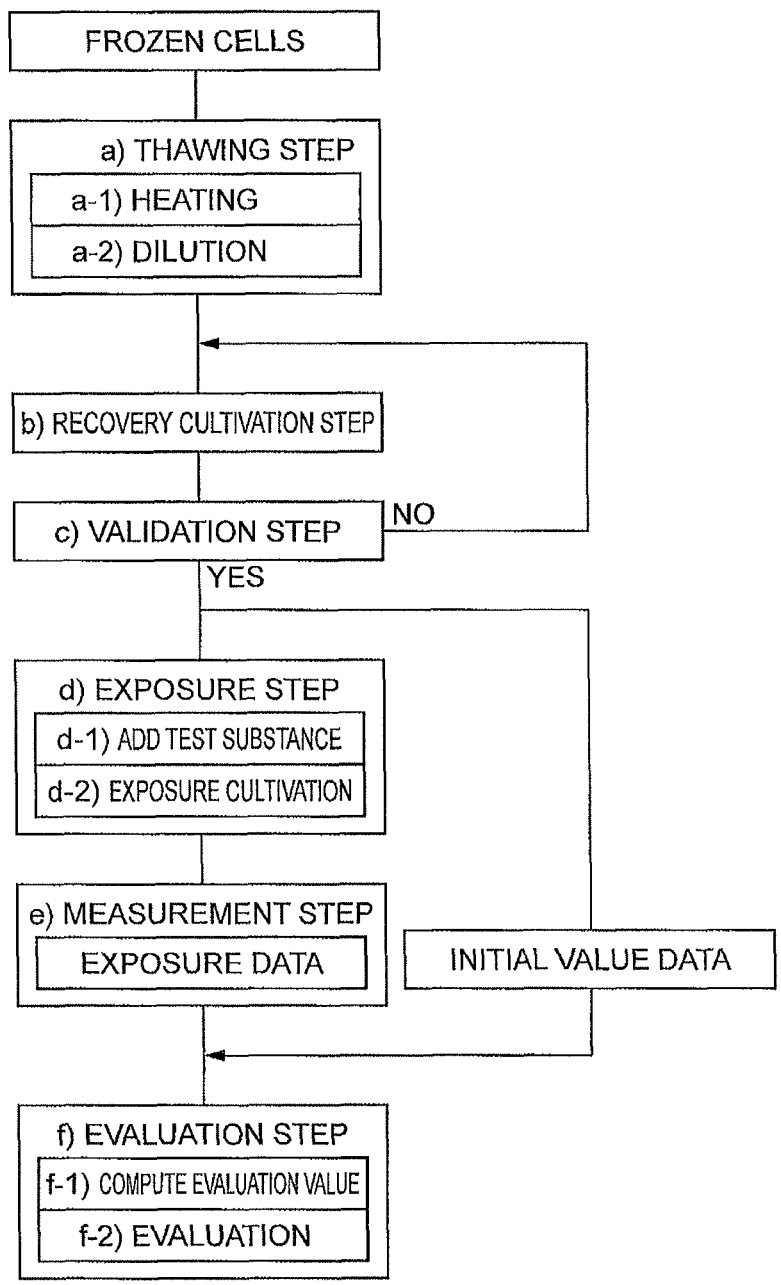
FIG. 26 is a flowchart for illustrating a method of evaluating a toxicity of a chemical substance using the algae in accordance with Example 5.

FIG. 26 is a flowchart for explaining the method for evaluating a toxicity of a chemical substance using algae in accordance with an embodiment. This embodiment comprises a thawing step (a), a recovery cultivation step (b), a validation step (c), an exposure step (d), a measurement step (e), and an evaluation step (f).

The thawing step (a) heats and thaws the algal cells frozen by the above-mentioned method and dilutes with a medium the cell suspension obtained by the thawing.

The thawing can be effected by slowly vibrating a cryo tube containing the frozen cells for about 120 to 150 sec in a water bath at 37° C., for example.

Subsequently, the thawed cell suspension is diluted with a medium. As mentioned above, there is a case where the frozen cell suspension contains a frost damage protectant such as dimethyl sulfoxide (DMSO), which makes it necessary to dilute the suspension immediately after thawing in order to lessen the cytotoxicity of the frozen cell suspension. The dilution may be a factor of 10 with an OECD medium, for example. For preventing the osmotic pressure from changing drastically, the medium is added slowly over a time of about 1 min.

The recovery cultivation step (b) cultivates the algal cells obtained by the thawing step (a) so that the algal cells recover from influences of freezing and thawing. As indicated by a comparative example which will be explained later, without the recovery cultivation step, the algal cells fail to recover fully from damages caused by freezing and thawing, so that their delayed luminescence yields a light emission pattern different from that of unfrozen algal cells, thereby lowering the light emission quantity. The toxicity of the chemical substance cannot be evaluated appropriately unless the frozen and thawed algal cells exhibit the same light emission pattern and light emission quantity as those of unfrozen algal cells. As indicated by examples which will be explained later, performing the recovery cultivation step in addition to the thawing step (a) allows the frozen and thawed algal cells to exhibit the same light emission pattern and light emission quantity as those of unfrozen algal cells, thereby solving this problem. The recovery cultivation is performed for 1 to 2 hr under a condition with a temperature of 25±0.5° C. and an illuminance of 50 to 55 $\mu mol \cdot m^{-2} \cdot s^{-1}$, for example.

The validation step (c) takes a part of the algal cells after the recovery cultivation step (b), dilutes it with a medium, measures delayed luminescence of the algal cells, and adopts thus obtained light emission quantity as initial value data. This step validates that the algal cells have fully recovered from influences of freezing and thawing by the recovery cultivation step (b) and acquires initial value data for use when evaluating the toxicity later.

The purpose for further diluting the algal cells is to lessen the toxicity of the frost damage protectant. There is a case where the frozen cell suspension contains about 5 to 10% of the frost damage protectant. In this case, about 10-fold dilution in the thawing step yields a frost damage protectant concentration of about 0.5 to 1%, while the recovery step has been found possible even in the presence of the frost damage protectant at this concentration. For preventing the chemical substance toxicity evaluation from being affected, however, a further 10-fold dilution is required to be performed after the cultivation, so as to lower the concentration of the frost damage protectant.

The delayed luminescence can be measured by known devices and methods such as those described in International Publication No. 2005/062027, for example.

When the light emission quantity measured by the validation step (c) is a predetermined value, this value can be adopted as the initial value data, so as to proceed to the subsequent exposure step (d). As the predetermined value to become a reference for determination, a preset value or a value individually set for the frozen cells can be utilized. For example, a manufacturer can set a value at the time of producing the frozen cells. An example of the predetermined value is at least 90% of the light emission quantity of unfrozen algal cells. At this value or below, it can be determined that the light emission quantity is insufficient, so that the algal cells have not recovered fully.

When the light emission quantity measured by the validation step (c) does not reach the predetermined value, the recovery cultivation step (b) is continued, and the validation step is performed again after the lapse of a predetermined time (e.g., 30 min), so as to see whether or not the measured amount reaches the predetermined value.

The exposure step (d) mixes the algal cells seen to have recovered fully from influences of freezing and thawing according to the validation step (c) with a solution containing a test substance, so as to produce an exposure sample and cultivates the exposure sample.

For producing the exposure sample, 9 parts by volume of the solution containing the test substance is added to 1 part by volume of the algal cells, for example. This operation dilutes the algal cells by a factor of 10 in order to avoid the frost damage protectant from affecting the chemical substance toxicity evaluation as mentioned above. Since the solution containing the test substance can be added by a large amount, even chemical substances which are hard to dissolve in water can be evaluated. A plurality of exposure samples can be prepared with various concentrations of the test substance. A control sample may be produced by mixing only a solvent dissolving the test substance with the algal cells. Measuring control data with the control sample and computing the evaluation value can evaluate the toxicity of the test substance more accurately.

The exposure sample is cultivated under a condition with a temperature of 25±0.5° C. and an illuminance of 50 to 55 $\mu mol \cdot m^{-2} \cdot s^{-1}$, for example. The cultivation time, which is not restricted in particular as long as it is such a time that the test substance affects the algal cells, is 8 hr, for example, preferably 24 hr. For facilitating the measurement of delayed luminescence, a test tube which can be used as it is for measuring the delayed luminescence can be employed as a culture vessel for the exposure sample. For minimizing the variability in illuminance among test tubes, increasing the stirring efficiency, and raising the cell proliferation rate of algae in this case, roller tube culture using a rotator together with an orbital shaker is preferably performed.

The measurement step (e) measures the delayed luminescence of the exposure sample after the exposure step (d) and adopts thus obtained light emission quantity as exposure data. As mentioned above, the delayed luminescence can be measured by known devices and methods such as those described in International Publication No. 2005/062027, for example. More specifically, after irradiating the sample with excitation light (680 nm, 20 $\mu mol \cdot m^{-2} \cdot s^{-1}$) for 1 sec, the delayed luminescence emitted from the sample is detected by a photomultiplier and recorded at intervals of 100 msec for 60 sec after the completion of excitation, and the sum of delayed luminescence quantities from 1.1 sec to 60 sec after the completion of excitation is adopted as the exposure data.

The evaluation step (f) computes an evaluation value according the initial value data and exposure data and evaluates the toxicity of the test substance according to the evaluation value. The delayed luminescence is known to lower the light emission quantity in correlation with the growth inhibition of algal cells. When the exposure data is lower than the initial value data, it can be evaluated that the test substance is toxic. More specifically, a sample (X) containing a detrimental substance to become a subject to be evaluated and a sample (Y) containing no detrimental substance are measured as exposure samples, the increase rate of each of them is computed from the following expression 1, the increase rate of X is compared with that of Y, and the amount of decrease in X with respect to Y is computed from the following expression 2 and adopted as an index for toxicity.

Increase rate=(ln(exposure data)−ln(initial data))/ (cultivation time).     Expression 1:

Rate of decrease=(increase rate of Y−increase rate of X)/increase rate of Y×100.     Expression 2:

The following will illustrate a comparative example and examples of the method for preparing algal cells. Each experiment was performed with n=3.

Comparison of Cells in the Stationary Phase and Cells in the Logarithmic Growth Phase Example 1

Figure 3:
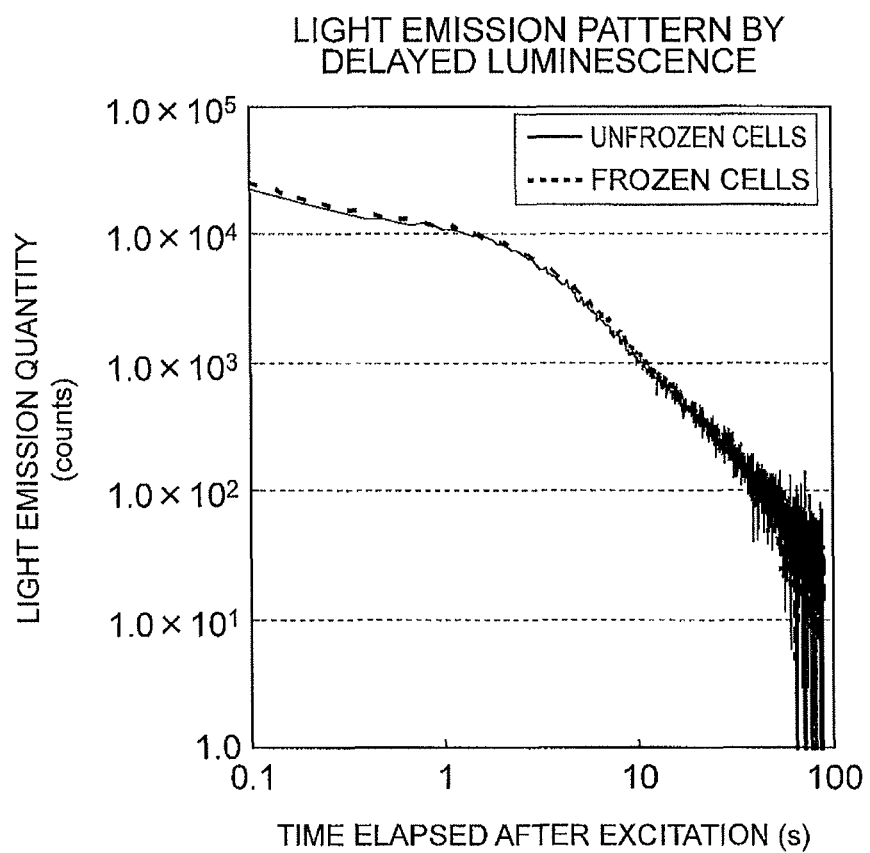
FIG. 3 is a graph representing light emission patterns by delayed luminescence of the thawed green algae cells frozen in the logarithmic growth phase (Example 1) and the unfrozen green algae cells.

As cells to be frozen, cells in the logarithmic growth phase (at a cell density of 180×10$^4$ cells/mL) of green algae preserved as strain No. NIES-35 in National Institute for Environmental Studies (NIES-35 strain) were used. As a culture solution for cultivating the green algae, 100 mL of an OECD medium was used. The culture solution containing the cells was centrifuged (at 1000 G for 5 min), the supernatant was completely removed therefrom by an aspirator, the remnant was suspended again in several mL of a new culture solution, and a part thereof was taken, so as to count the number of cells. Thereafter, the culture solution was added thereto, so as to yield a density of 4000×10$^4$ cells/mL. The added culture solution was mixed with an equivalent quantity of a 10% DMSO solution (frost damage protectant), so as to yield a final cell density of 2000×10$^4$ cells/mL and a final DMSO density of 5%. After being left at room temperature for 15 min, the mixture was dispensed into a cryo tube, wrapped with a shock-absorbing material, contained in a freezer container equipped with a protective material, and preserved at −80° C. for a maximum of 180 days. The cells were thawed, cultivated, and subjected to a growth test, and their delayed luminance was measured. FIG. 1 illustrates thus obtained growth curve. FIG. 3 illustrates a pattern of delayed luminance of the cultivated cells together with a pattern of delayed luminescence of unfrozen cells.

Comparative Example 1

Figure 2:
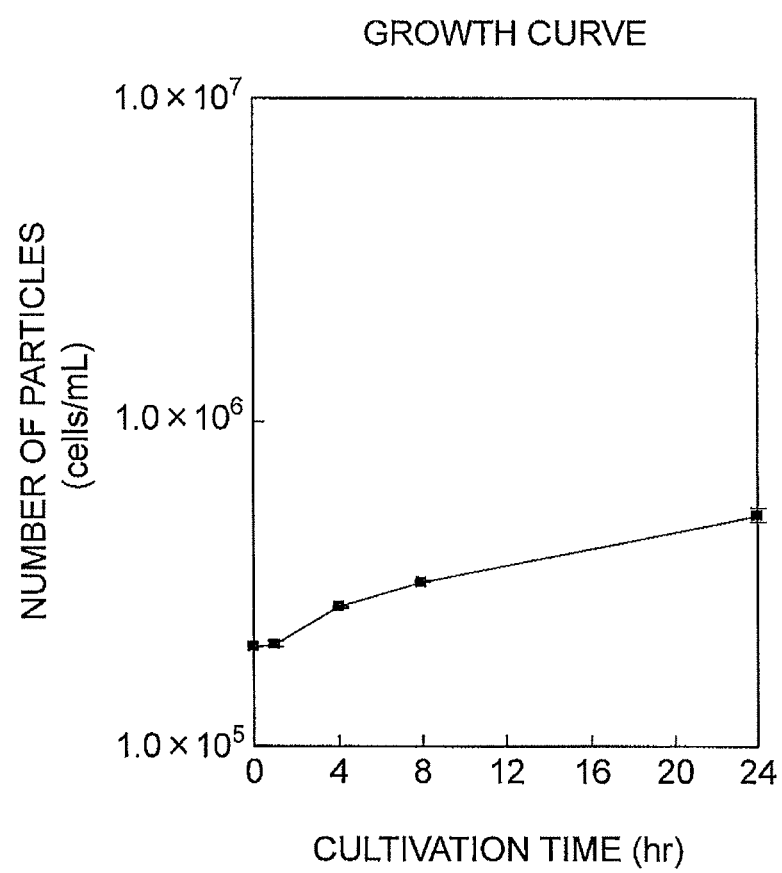
FIG. 2 is a graph illustrating a growth curve of the thawed green algae cells frozen in the stationary phase (Comparative Example 1)

As cells to be frozen, cells in the stationary phase (at a cell density of 332×10$^4$ cells/mL) of green algae preserved as strain No. NIES-35 in National Institute for Environmental Studies (NIES-35 strain) were used. The cells were prepared, frozen, thawed, cultivated, and subjected to the growth test by the same method as that of Example 1 except that the cells in the stationary phase were used in place of the cells in the logarithmic growth phase. FIG. 2 illustrates thus obtained growth curve.

When the cells in the logarithmic growth phase were used as the cells to be frozen, the cultivated thawed cells grew smoothly, thereby yielding logarithmic growth (FIG. 1). When the cells in the stationary phase were used as the cells to be frozen, by contrast, the growth of the cultivated thawed cells was inferior (FIG. 2).

Study on Whether or not to Remove the Supernatant

Example 2

Figure 4:
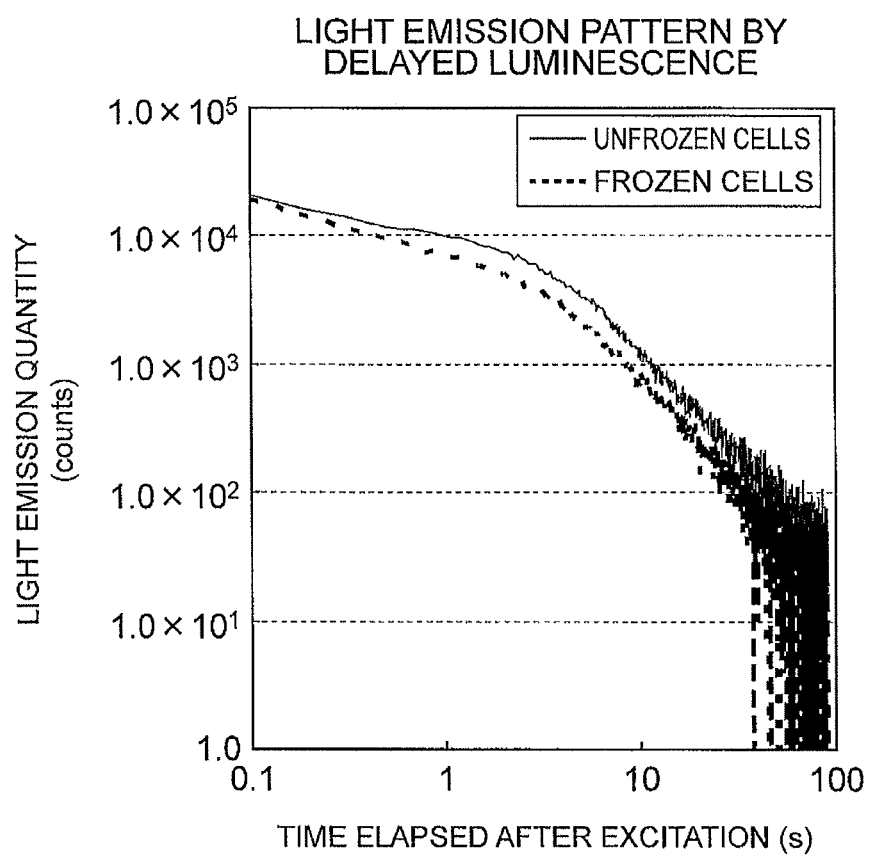
FIG. 4 is a graph representing light emission patterns by delayed luminescence of the thawed green algae cells frozen in the logarithmic growth phase (Example 2) and the unfrozen green algae cells.
Figure 5:
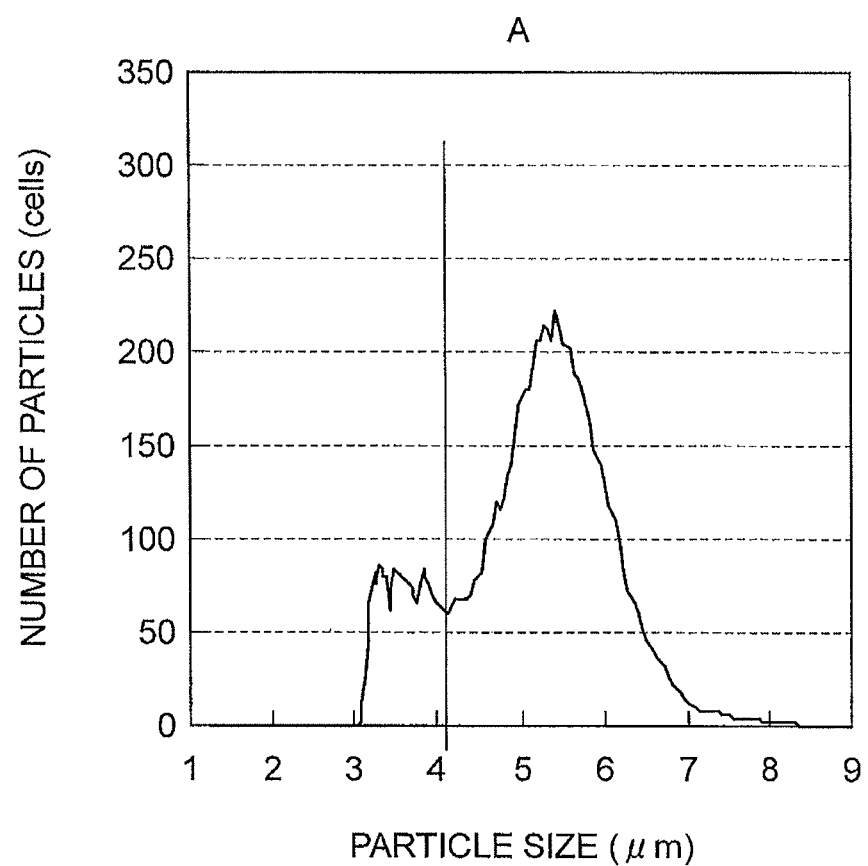
FIG. 5 is a graph illustrating a particle size distribution curve of NIES-35 strain cells (A)
Figure 6:
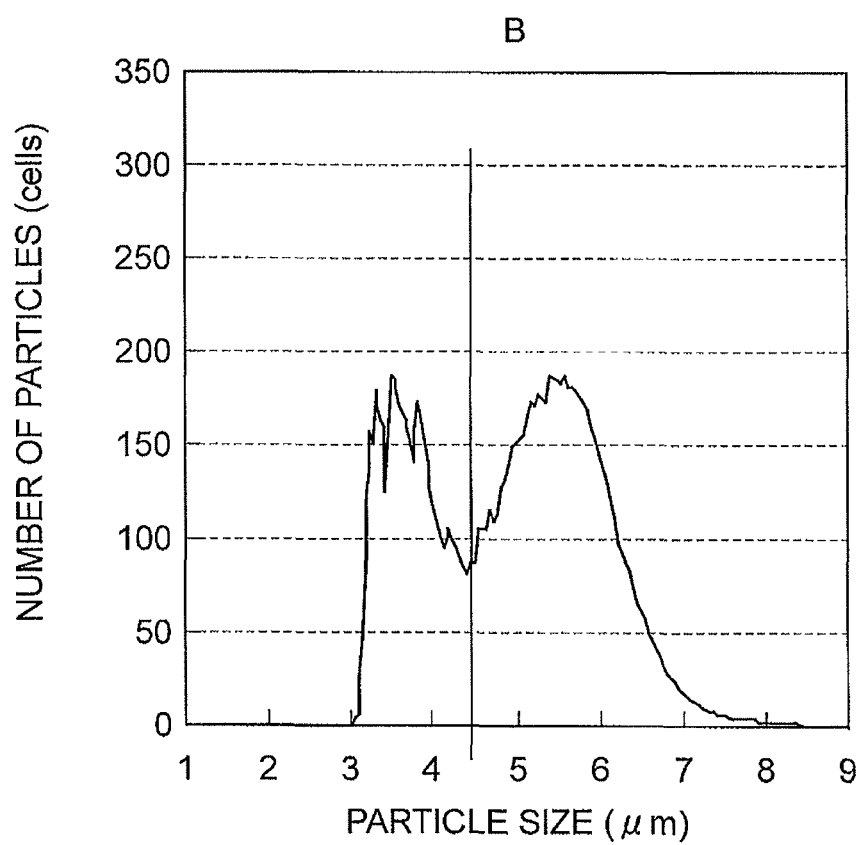
FIG. 6 is a graph illustrating a particle size distribution curve of NIES-35 strain cells (B)
Figure 7:
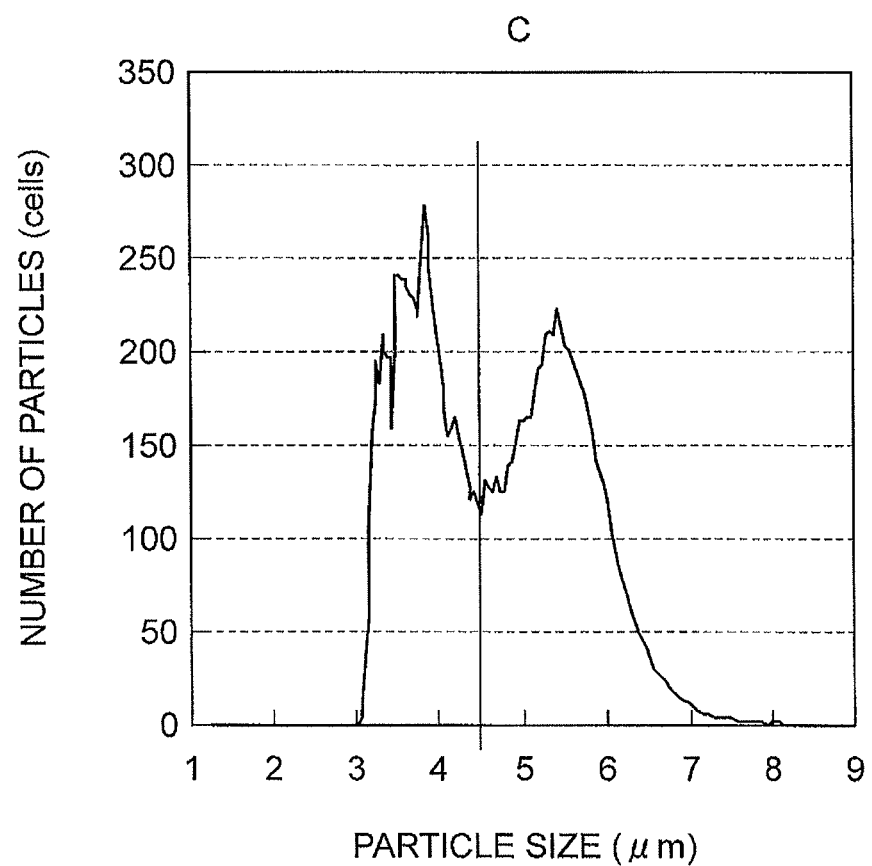
FIG. 7 is a graph illustrating a particle size distribution curve of NIES-35 strain cells (C)
Figure 8:
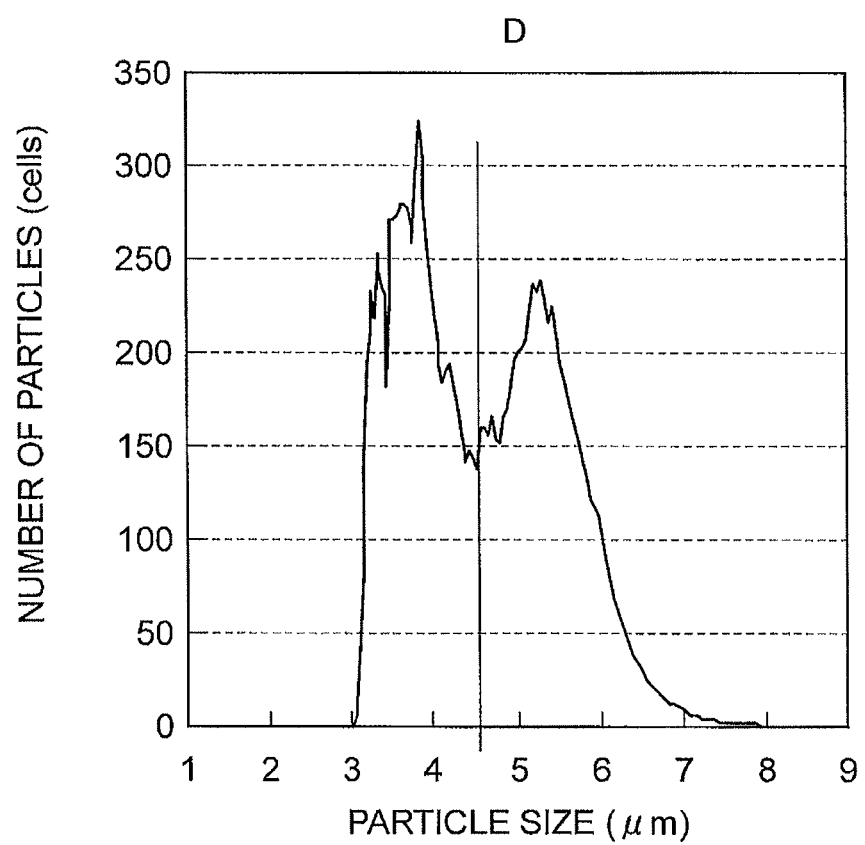
FIG. 8 is a graph illustrating a particle size distribution curve of NIES-35 strain cells (D)

As cells to be frozen, cells in the logarithmic growth phase (at a cell density of 180×10$^4$ cells/mL) of green algae preserved as strain No. NIES-35 in National Institute for Environmental Studies (NIES-35 strain) were used. As the culture solution, 100 mL of the same culture solution as that of Example 1 was used. The culture solution containing the cells was centrifuged, the resulting supernatant was spilled out to leave several mL thereof, and the precipitated cells were suspended again in the remaining culture solution. A DMSO solution and a new medium were further added to the suspension, so as to yield a final cell density of $2000 \times 10^4$ cells/mL and a final DMSO density of 5%. After being left at room temperature for 15 min, the mixture was dispensed into a cryo tube and frozen and preserved at −80° C. As in Example 1, the cells were thawed and cultivated, and their delayed luminescence was measured. FIG. 4 illustrates a pattern of delayed luminance of the cultivated cells together with a pattern of delayed luminescence of unfrozen cells.

In Example 1 in which the culture solution cultivating the cells was centrifuged and the supernatant thus separated from the cells was completely removed when preparing cells before freezing, the pattern of delayed luminescence coincided with that of delayed luminescence of unfrozen cells. In Example 2 in which the culture solution supernatant was not completely removed, by contrast, the pattern of delayed luminescence slightly shifted from that of delayed luminescence of unfrozen cells, thereby indicating it preferable to completely remove the culture solution supernatant when preparing cells before freezing.

Determination of Whether the Particle Size of Cells is Good or not

Example 3

As cells, those of green algae preserved as strain No. NIES-35 in National Institute for Environmental Studies (NIES-35 strain) were used. The green algae cells were cultivated from the logarithmic growth phase to the stationary phase, so that the cells in four growth stages composed of the following A to C cell groups with different cultivation times in the logarithmic growth phase and D cell group in the stationary phase were used:

A: cultivation time of 70 hr (cell density of $180 \times 10^4$ cells/mL)

B: cultivation time of 72 hr (cell density of $230 \times 10^4$ cells/mL)

C: cultivation time of 74 hr (cell density of $280 \times 10^4$ cells/mL)

D: cultivation time of 76 hr (cell density of $332 \times 10^4$ cells/mL)

FIGS. 5 to 8 illustrate respective particle size distribution curves of the A to D cell groups. Each of the particle size distribution curves of the A to D cell groups clearly exhibited a bimodal distribution. In each chart, a line is drawn at a position where the particle size is at a valley value. The following Table 1 lists the valley value and the ratios of cells divided into two at the valley value in each of the respective particle size distributions of A to D cell groups. Table 1 refers to cells having particle sizes larger and smaller than the valley value as "larger cell" and "smaller cell," respectively, and lists the respective ratios of the numbers of "larger cells" and "smaller cells" in each of the A to D cell groups.

TABLE 1

| | VALLEY VALUE (μm) | NUMBER OF CELLS (SMALLER CELLS: %) | NUMBER OF CELLS (LARGER CELLS: %) |
|---|---|---|---|
| A | 4.12 | 24 | 76 |
| B | 4.40 | 45 | 55 |
| C | 4.52 | 56 | 44 |
| D | 4.52 | 59 | 41 |

As FIGS. 5 to 8 and Table 1 indicate, the number of cells having smaller particle sizes increased their ratio as the cell density became higher, so that the cells having larger particle sizes were in majority in A and B, while the cells having smaller particle sizes were in majority in C and D. In the A and B cell groups, the valley value was about 4.40 μm or less, and a majority of the cells had particle sizes not smaller than the valley value. Specifically, the numbers of cells having particle sizes not smaller than the valley value were 76% and 55% in A and B, respectively.

Table 2 lists particle sizes at two peaks (peaks at larger and smaller particle sizes) in each of the bimodal particle size distribution curves of A to D as "peak 1" and "peak 2" for the smaller and larger particle sizes, respectively. Table 2 also lists the ratio of number of cells at each peak (peak value ratio) when the total of the number of cells at the peak 1 and the number of cells at the peak 2 is assumed to be 100%. Here, the cells having a particle size of the peak particle size±0.02 μm were measured as "cells at the peak." The particle sizes at the peak 1, peak 2, and valley value were determined by the particle size data computed by a particle size distribution analyzer of an electrical sensing zone type.

TABLE 2

| | PEAK PARTICLE SIZE (PEAK 1: μm) | PEAK PARTICLE SIZE (PEAK 2: μm) | PEAK VALUE RATIO (PEAK 1: %) | PEAK VALUE RATIO (PEAK 2: %) |
|---|---|---|---|---|
| A | 3.31 | 5.43 | 28 | 72 |
| B | 3.49 | 5.43 | 50 | 50 |
| C | 3.83 | 5.43 | 56 | 44 |
| D | 3.83 | 5.29 | 58 | 42 |

As FIGS. 5 to 8 and Table 2 indicate, the peak value ratio of the larger-particle-size peak (peak 2) tended to be higher as the cell density was lower, so that the larger-particle-size peak (peak 2) value ratio was 50% or higher in the A and B cell groups.

Figure 9:
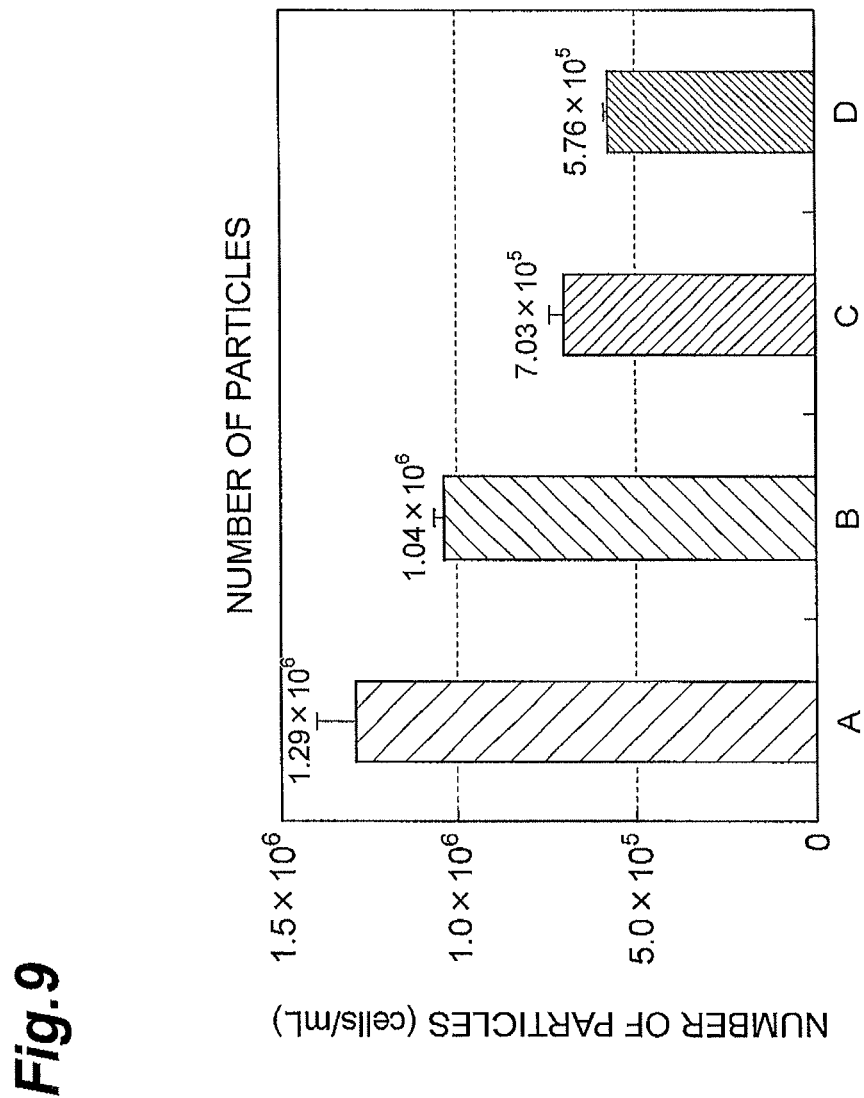
FIG. 9 is a graph representing the numbers of particles after cultivating the living cells of NIES-35 strain cells (A) to (D)
Figure 10:
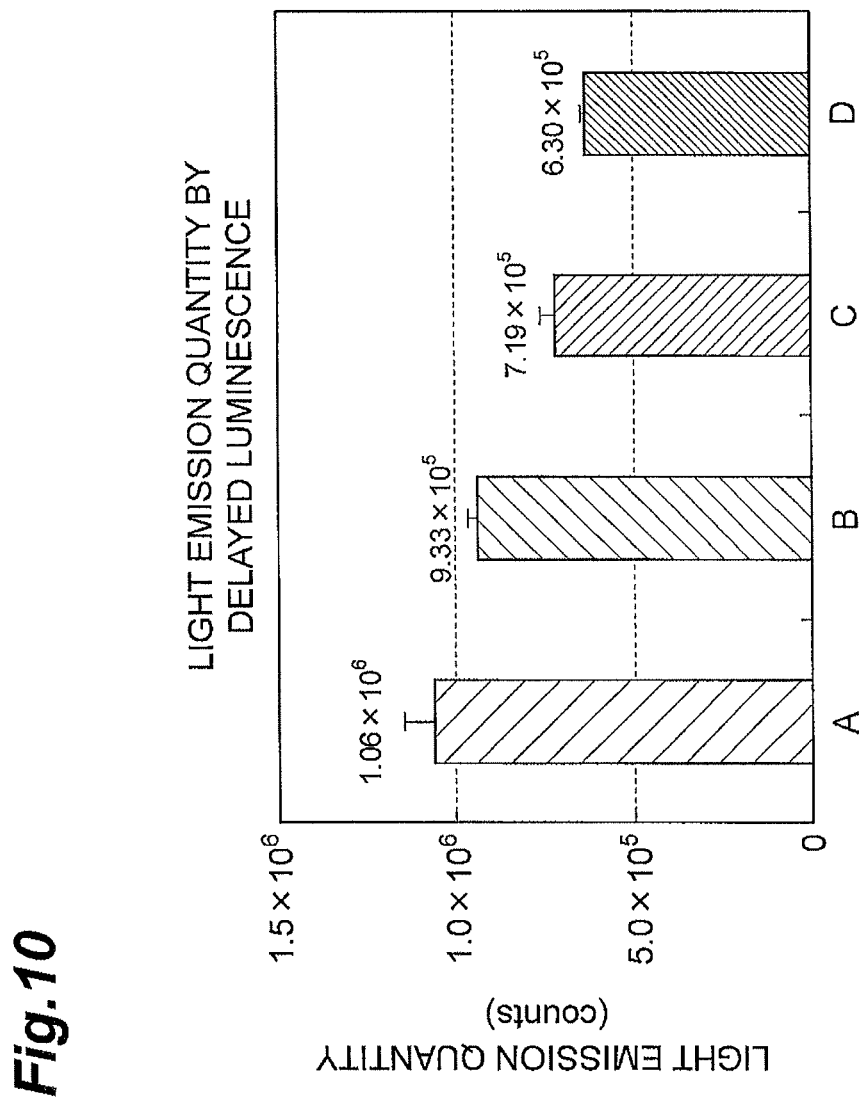
FIG. 10 is a graph representing light emission quantities by delayed luminescence after cultivating the living cells of NIES-35 strain cells (A) to (D)
Figure 11:
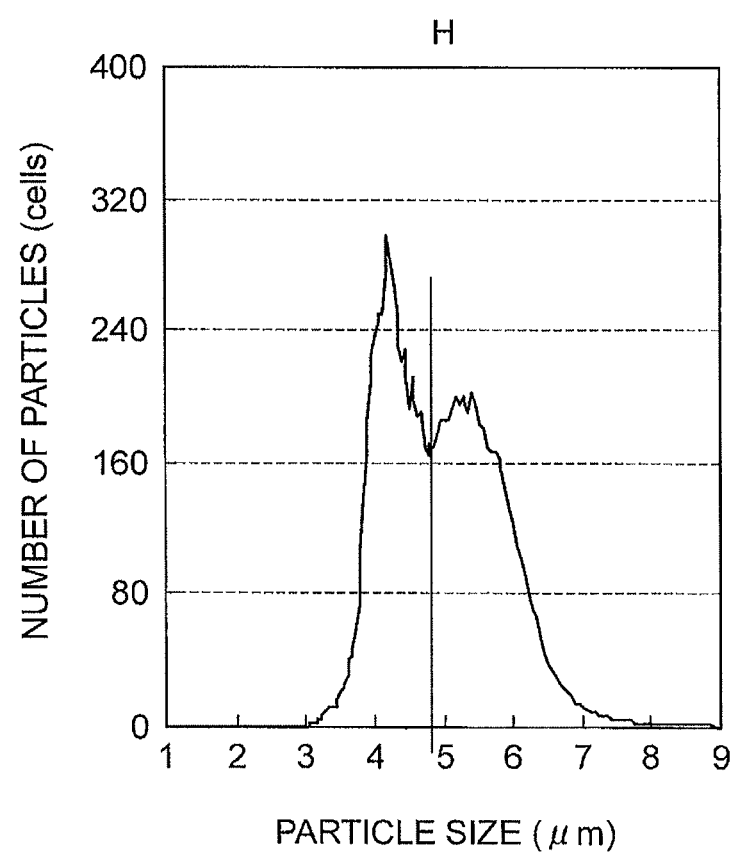
FIG. 11 is a graph illustrating a particle size distribution curve of ATCC-22662 strain cells (H)
Figure 12:
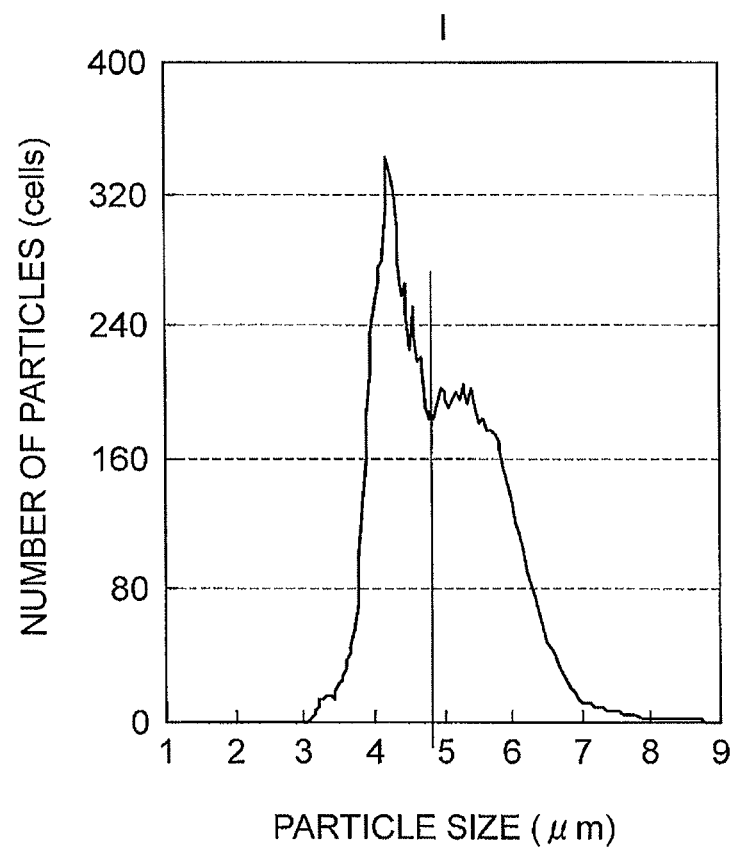
FIG. 12 is a graph illustrating a particle size distribution curve of ATCC-22662 strain cells (I)
Figure 13:
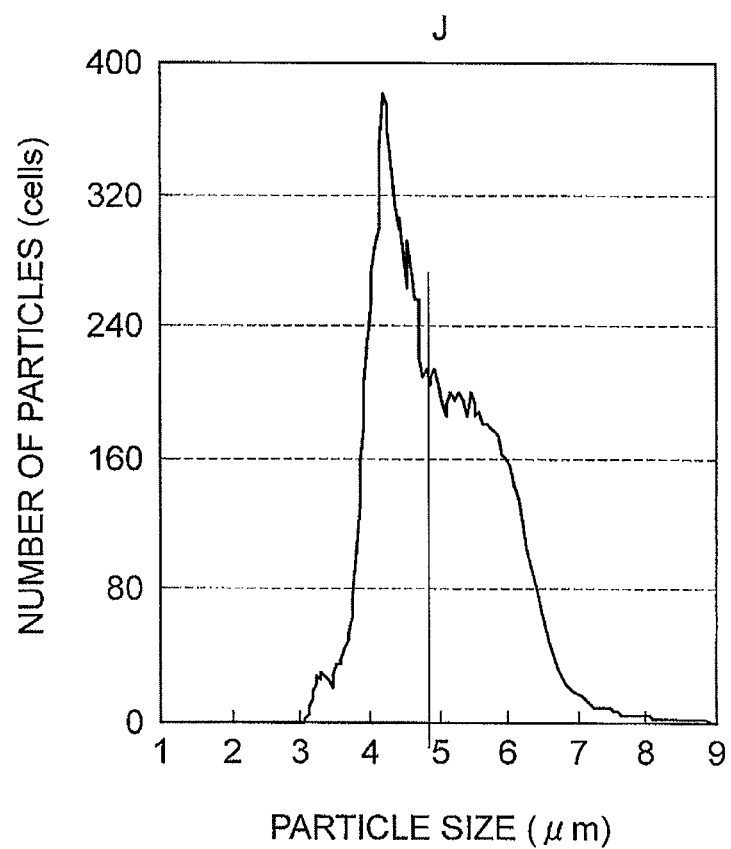
FIG. 13 is a graph illustrating a particle size distribution curve of ATCC-22662 strain cells (J)
Figure 14:
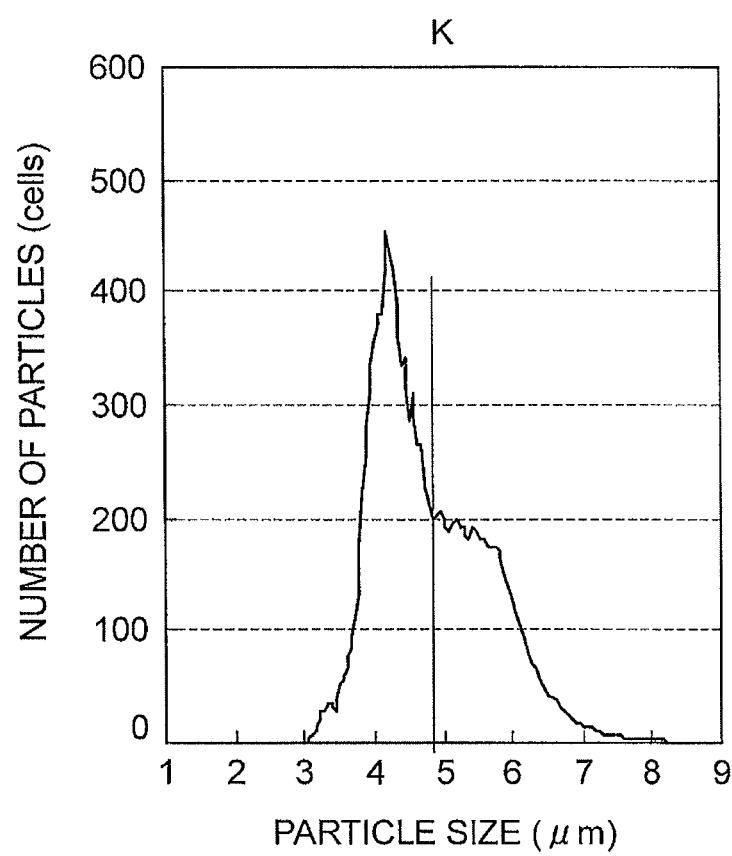
FIG. 14 is a graph illustrating a particle size distribution curve of ATCC-22662 strain cells (K)
Figure 15:
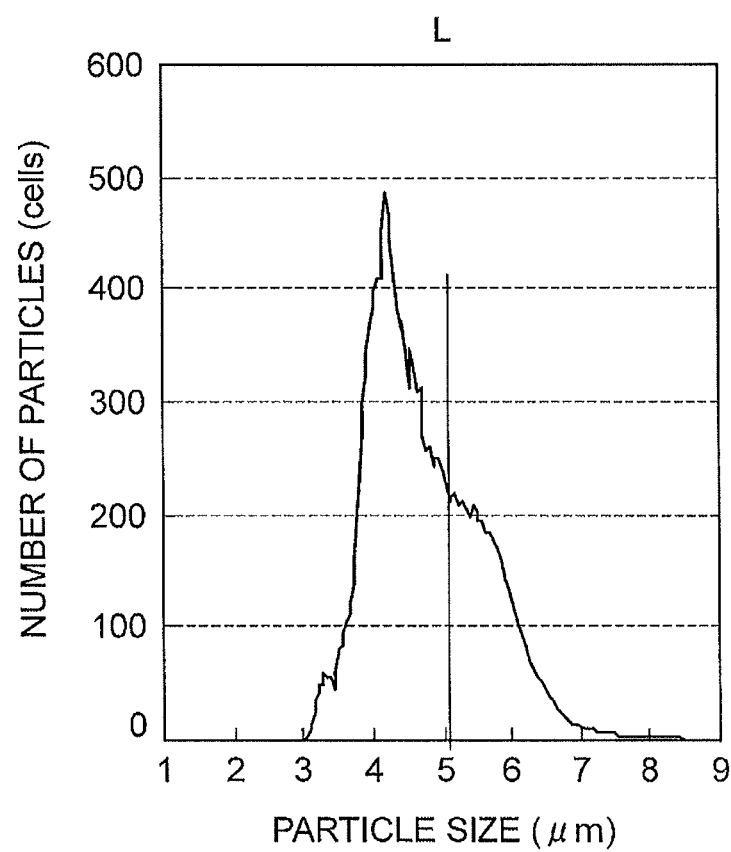
FIG. 15 is a graph illustrating a particle size distribution curve of ATCC-22662 strain cells (L)
Figure 16:
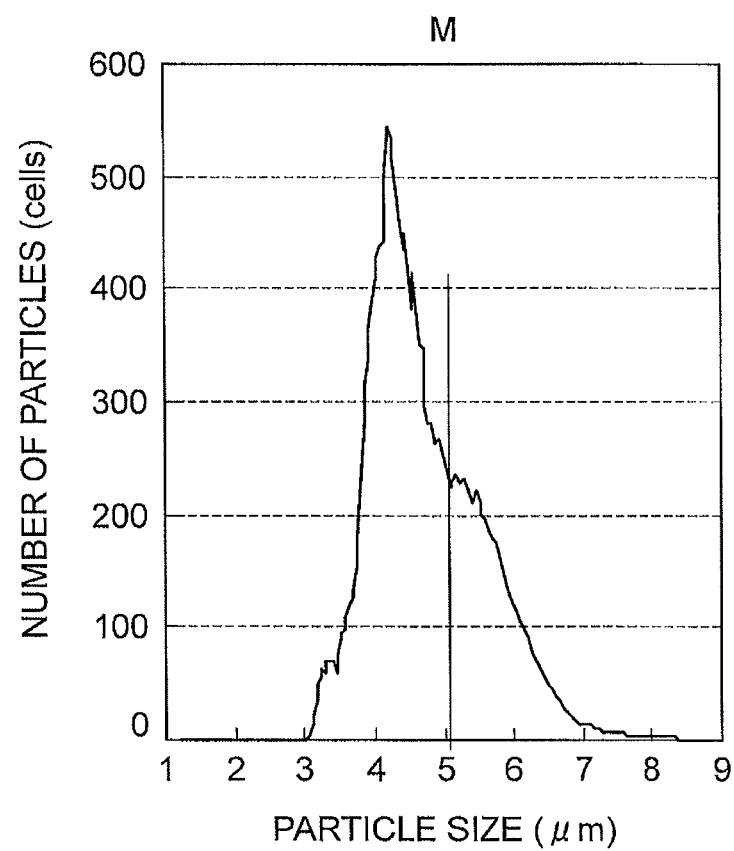
FIG. 16 is a graph illustrating a particle size distribution curve of ATCC-22662 strain cells (M)

Each of the A to D cell groups was prepared to yield an initial cell density of $20 \times 10^4$ cells/mL and cultivated for 24 hr, and then the number of particles of green algae cells and delayed luminescence were measured. FIGS. 9 and 10 illustrate the number of cells (cells/mL) and the light emission quantity (counts) obtained by delayed luminescence, respectively.

The number of cell particles after 24 hr was the largest in A with favorable growth and decreased successively in B, C, and D (FIG. 9). The light emission quantity by delayed luminescence was also the largest in A and decreased successively in B, C, and D (FIG. 10).

Example 4

As cells, those of green algae preserved as ATCC No. 22662 in the American Type Culture Collection (ATCC-22662 strain) were used. The green algae cells were cultivated from the logarithmic growth phase to the stationary phase, so that the cells in six growth stages composed of the following H to J cell groups with different cultivation times in the logarithmic growth phase and K to M cell groups in the stationary phase were used:

H: cultivation time of 72 hr (cell density of $233 \times 10^4$ cells/mL)

I: cultivation time of 74 hr (cell density of $256 \times 10^4$ cells/mL)

J: cultivation time of 76 hr (cell density of $281 \times 10^4$ cells/mL)

K: cultivation time of 78 hr (cell density of $312 \times 10^4$ cells/mL)

L: cultivation time of 80 hr (cell density of $352 \times 10^4$ cells/mL)

M: cultivation time of 82 hr (cell density of $391 \times 10^4$ cells/mL)

FIGS. 11 to 16 illustrate respective particle size distribution curves of the H to M cell groups. Each of the particle size distribution curves of the H and I cell groups clearly exhibited a bimodal distribution. In each chart, a line is drawn at a position where the particle size is at a valley value. The following Table 3 lists the valley value and the ratios of cells divided into two at the valley value in each of the respective particle size distributions of H to M cell groups. Table 3 refers to cells having particle sizes larger and smaller than the valley value as "larger cell" and "smaller cell," respectively, and lists the respective ratios of the numbers of "larger cells" and "smaller cells" in each of the H to M cell groups.

TABLE 3

| | VALLEY VALUE (μm) | NUMBER OF CELLS (SMALLER CELLS: %) | NUMBER OF CELLS (LARGER CELLS: %) |
|---|---|---|---|
| H | 4.78 | 52 | 48 |
| I | 4.78 | 54 | 46 |
| J | 4.87 | 58 | 42 |
| K | 4.87 | 65 | 35 |
| L | 5.10 | 74 | 26 |
| M | 5.10 | 75 | 25 |

As FIGS. 11 to 16 and Table 3 indicate, the number of cells having smaller particle sizes increased their ratio as the cell density became higher. In the H and I cell groups, the ratio of smaller cells was on a par with that of larger cells. In the H and I cell groups, at least 50% of the cells had particle sizes not smaller than about 4.5 μm also in the ATCC-22662 strain.

Table 4 lists particle sizes at two peaks (peaks at larger and smaller particle sizes) in each of the bimodal particle size distribution curves of H to M as "peak 1" and "peak 2" for the smaller and larger particle sizes, respectively. Table 4 also lists the ratio of number of cells at each peak (peak value ratio) when the total of the number of cells at the peak 1 and the number of cells at the peak 2 is assumed to be 100%. Here, the cells having a particle size of the peak particle size±0.02 μm were measured as "cells at the peak." The particle sizes at the peak 1, peak 2, and valley value were determined as in Example 3.

TABLE 4

| | PEAK PARTICLE SIZE (PEAK 1: μm) | PEAK PARTICLE SIZE (PEAK 2: μm) | PEAK VALUE RATIO (PEAK 1: %) | PEAK VALUE RATIO (PEAK 2: %) |
|---|---|---|---|---|
| H | 4.2 | 5.43 | 59 | 41 |
| I | 4.2 | 5.29 | 63 | 37 |
| J | 4.2 | 5.29 | 66 | 34 |
| K | 4.2 | 5.19 | 69 | 31 |
| L | 4.2 | 5.19 | 69 | 31 |
| M | 4.2 | 5.19 | 70 | 30 |

As FIGS. 11 to 16 and Table 4 indicate, the peak value ratio of the smaller-particle-size peak (peak 1) tended to be higher in the ATCC-22662 strain. The peak value ratio of the smaller-particle-size peak (peak 1) also tended to be greater as the cell density was higher.

Figure 17:
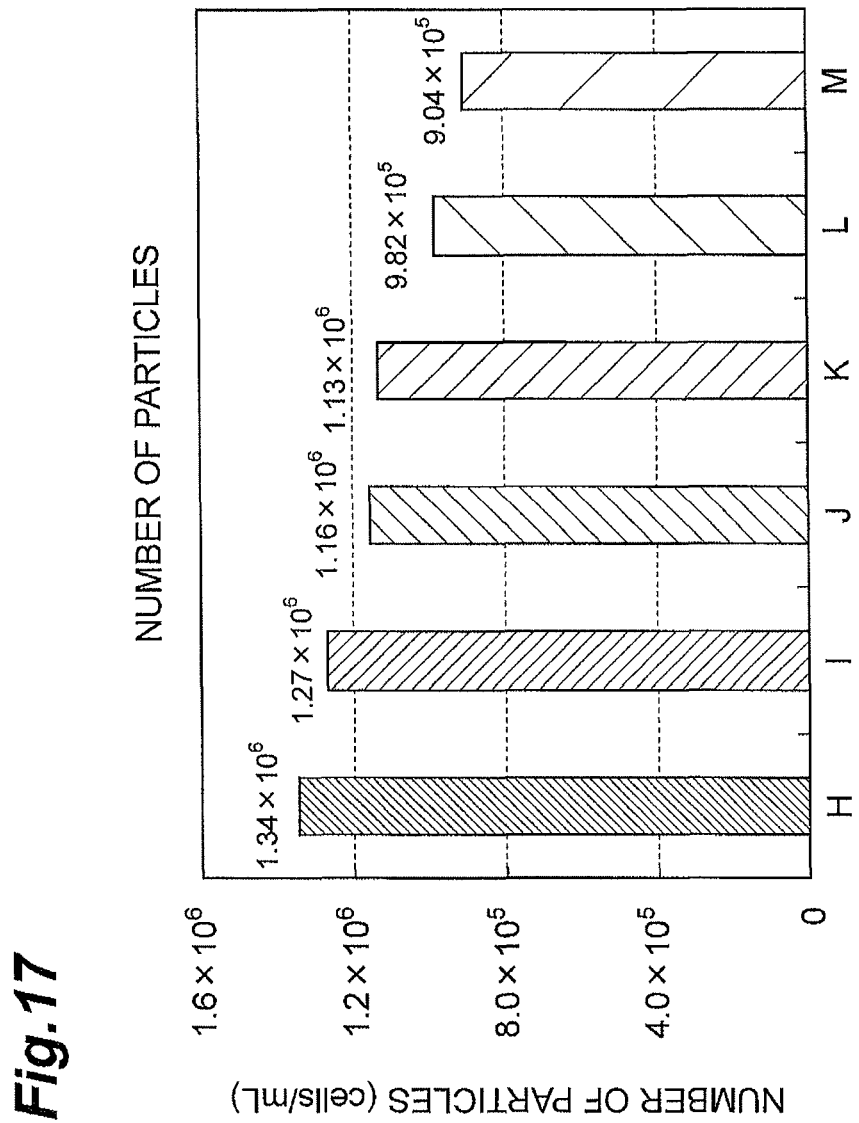
FIG. 17 is a graph representing the numbers of particles after cultivating the living cells of ATCC-22662 strain cells (H) to (M)
Figure 18:
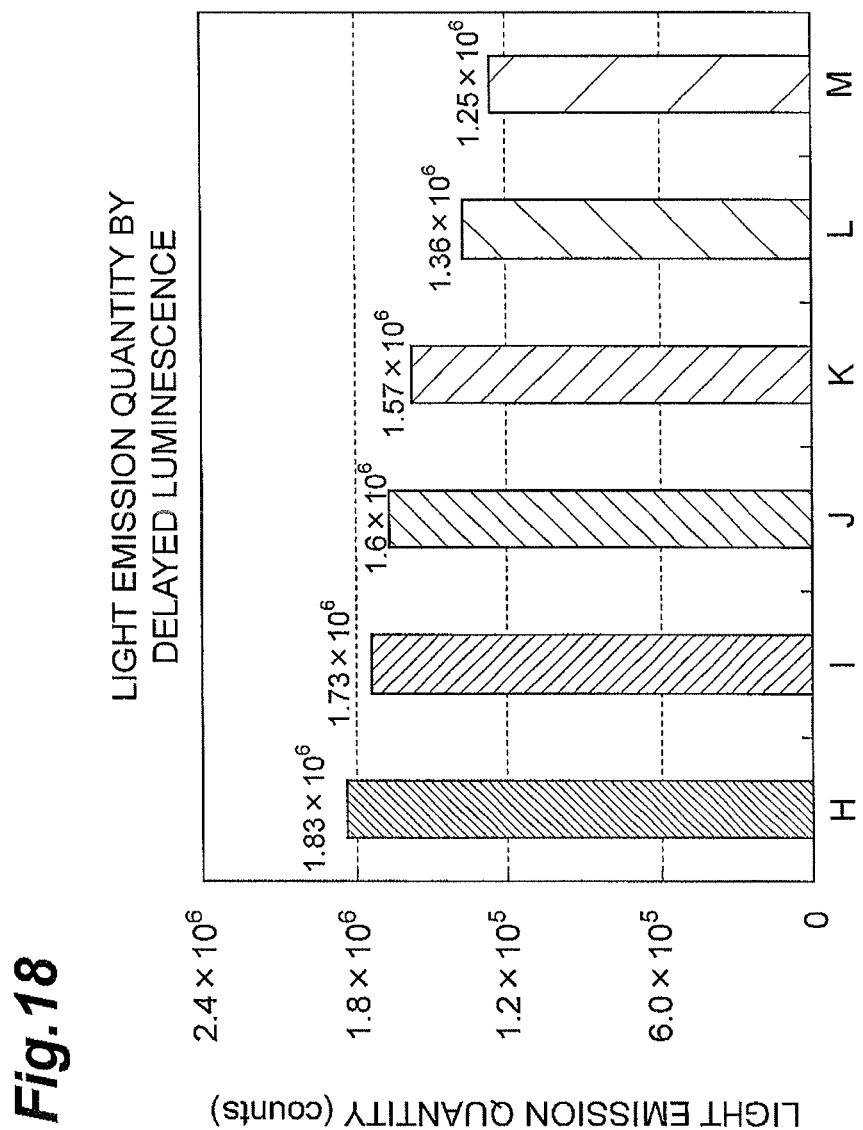
FIG. 18 is a graph representing light emission quantities by delayed luminescence after cultivating the living cells of ATCC-22662 strain cells (H) to (M)

Each of the H to M cell groups was prepared to yield an initial cell density of $20 \times 10^4$ cells/mL and cultivated for 24 hr, and then the number of particles of green algae cells and delayed luminescence were measured. FIGS. 17 and 18 illustrate the number of cells (cells/mL) and the light emission quantity (counts) obtained by delayed luminescence, respectively.

The number of cell particles after 24 hr was the largest in H with favorable growth and decreased successively in H to M (FIG. 17). The light emission quantity by delayed luminescence was also the largest in H and decreased successively in H to M (FIG. 18).

The following will illustrate a comparative example and an example concerning a toxicity evaluation method using algal cells.

Comparative Example 2

Using green algae (Pseudokirchneriella subcapitata) frozen under a condition with a cell density of $2000 \times 10^4$ cells/mL and a volume of 650 μL while containing a frost damage protectant (5% DMSO) by a standard procedure, delayed luminescence was measured by the following method. An OECD medium was used for a diluent.

(a) Thawing Step (a-1) Heating Step

The frozen green algae were completely thawed in about 120 to 150 sec in a cryo tube slowly vibrated in a water bath at 37° C. Within a clean bench, 620 μL of the cell suspension was taken into a glass tube by mild pipetting with a pipette having a thicker tip.

(a-2) Dilution Step

Into the glass tube, 5580 μL (10-fold dilution) of the OECD medium was slowly introduced. For preventing the osmotic pressure from changing drastically, the medium was added slowly over a time of about 1 min. After adding the medium, the mixture was left to stand still for about 5 to 10 min within the bench.

(c) Validation Step

A part of the sample having completed the dilution step (a-2) was taken and diluted by a factor of 10, so as to prepare an initial value sample. The delayed luminescence of the initial value sample was measured. The number of cells was determined by particle measurement. The number of living cells was counted by a colony method. The measurement of delayed luminescence, determination of the number of particles, and counting of the colony survival rate were also performed with unfrozen green algae.

Figure 19:
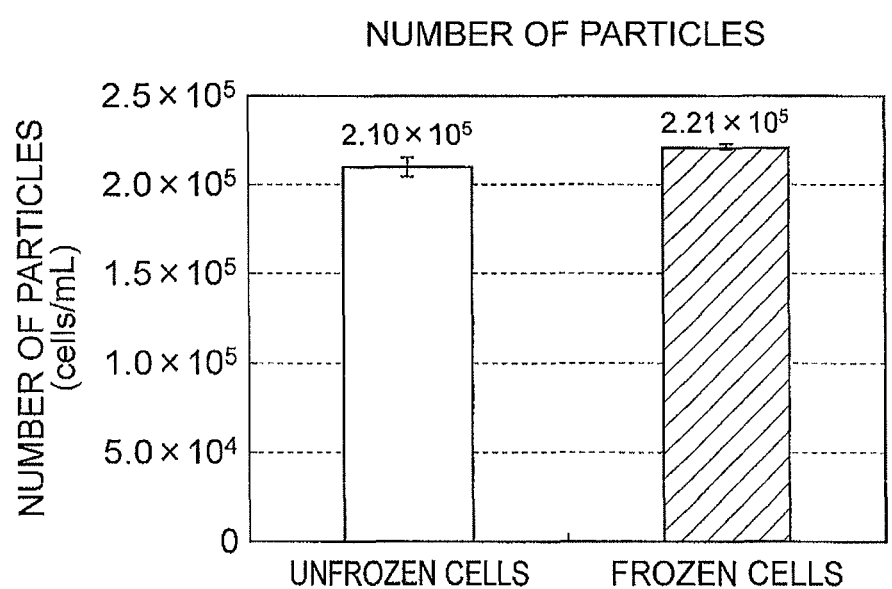
FIG. 19 is a graph representing the numbers of particles of frozen and thawed green algae (Comparative Example 2) and unfrozen green algae.
Figure 20:
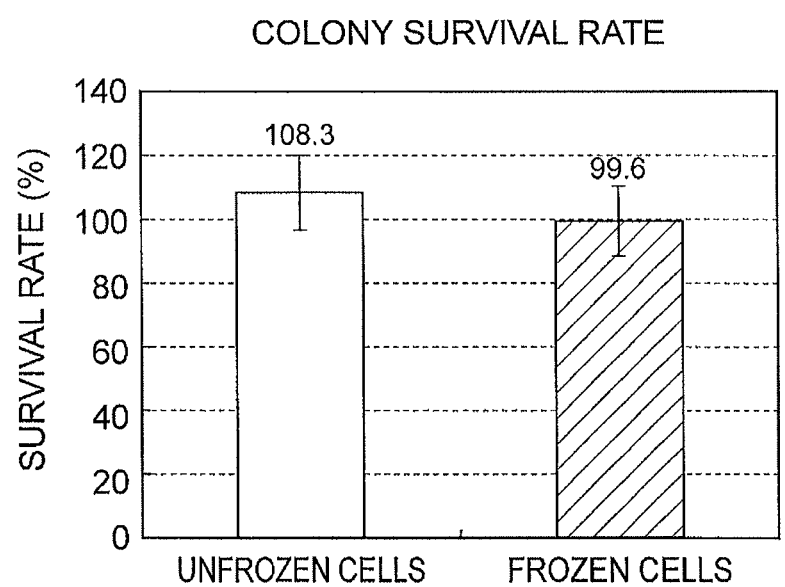
FIG. 20 is a graph representing colony survival rates of the frozen and thawed green algae (Comparative Example 2) and unfrozen green algae.

FIG. 19 is a graph illustrating the numbers of particles of the frozen and thawed green algae and the unfrozen green algae, while FIG. 20 is a graph illustrating the colony survival rates of the frozen and thawed green algae and the unfrozen green algae. As can be seen from FIGS. 19 and 20, the number of particles and colony survival rate of the frozen and thawed green algae in the validation step (c) hardly differ from those of the unfrozen green algae and appear to have recovered from influences of freezing and thawing to an appropriate state.

Figure 21:
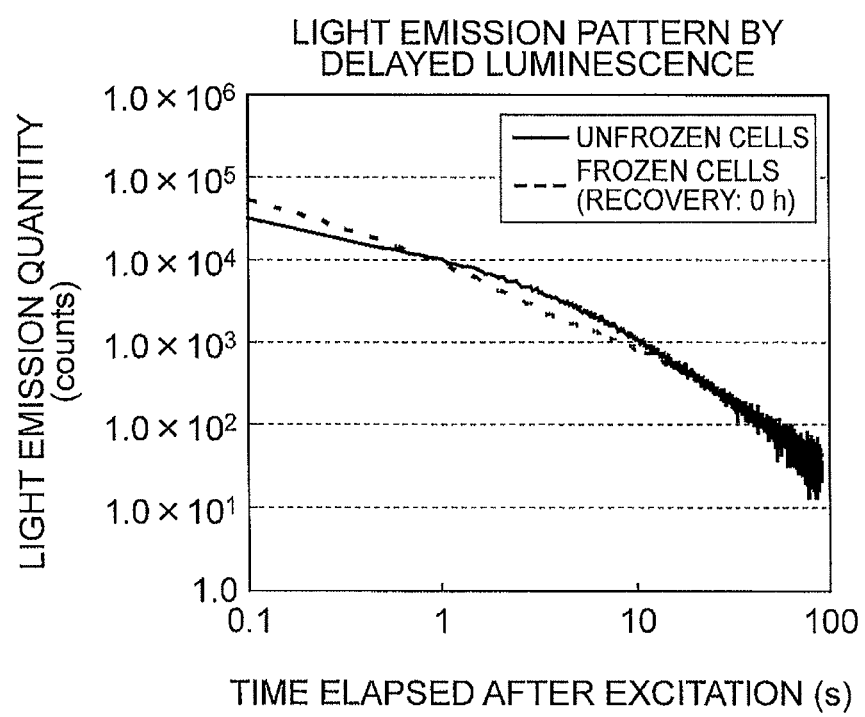
FIG. 21 is a graph representing light emission patterns by delayed luminescence of the frozen and thawed green algae (Comparative Example 2) and unfrozen green algae.
Figure 22:
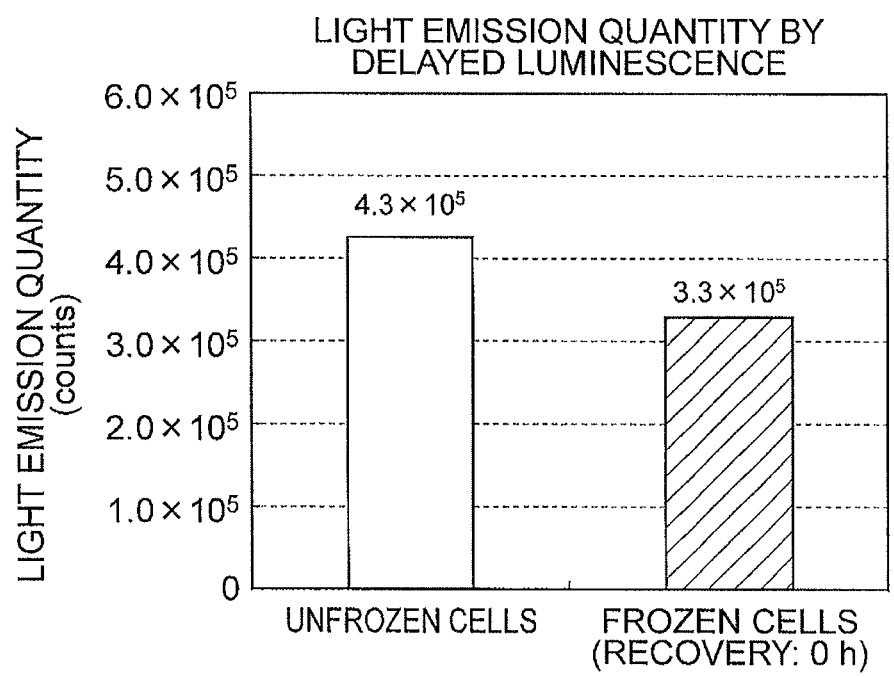
FIG. 22 is a graph representing light emission quantities (integrated values) of the frozen and thawed green algae (Comparative Example 2) and unfrozen green algae.

However, from FIG. 21 which is a graph illustrating light emission patterns of delayed luminescence, it is seen that the frozen and thawed green algae and the unfrozen green algae exhibit light emission patterns different from each other. When the light emission patterns differ from each other, the frozen and thawed algae cannot be evaluated on a par with the unfrozen algae in the subsequent chemical substance toxicity evaluation. FIG. 22, which is a graph representing light emission quantities (integrated values) from 1.1 to 60 sec after turning off the excitation light, shows that the light emission quantity of the frozen green algae is lower than that of the unfrozen green algae, i.e., about 77% of the latter. Since delayed luminescence is known to decrease in correlation with the growth inhibition of algae, algal cells whose light emission quantity has already been lowered by freezing and thawing from that before freezing is expected to have already incurred the growth inhibition, whereby the chemical substance to be evaluated cannot be evaluated appropriately in terms of toxicity even when exposed. Therefore, the method of the above-mentioned Comparative Example 2 is not suitable for the method for evaluating a chemical substance utilizing delayed luminescence of algae.

Example 5

(a) The thawing step was performed by the same method as that of Comparative Example 2.

(b) Recovery Cultivation Step

The sample prepared by the thawing step (a) was cultivated for 1 or 2 hr at a temperature of 25±0.5° C. under an illuminance of 50 to 55 µmol·m$^{-2}$·s$^{-1}$.

(c) Validation Step

A part of the sample having completed the recovery cultivation step (b) was taken and diluted, so as to prepare an initial value sample. The delayed luminescence of the initial value sample was measured. The measurement of delayed luminescence was also performed with unfrozen green algae.

Figure 23:
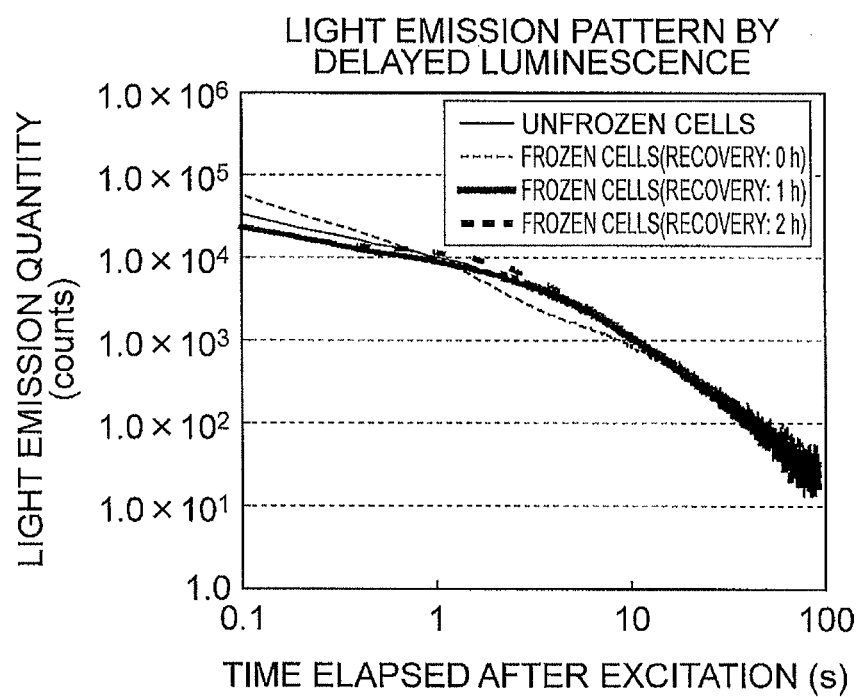
FIG. 23 is a graph representing light emission patterns by delayed luminescence of frozen and thawed green algae (Example 5) and unfrozen green algae.
Figure 24:
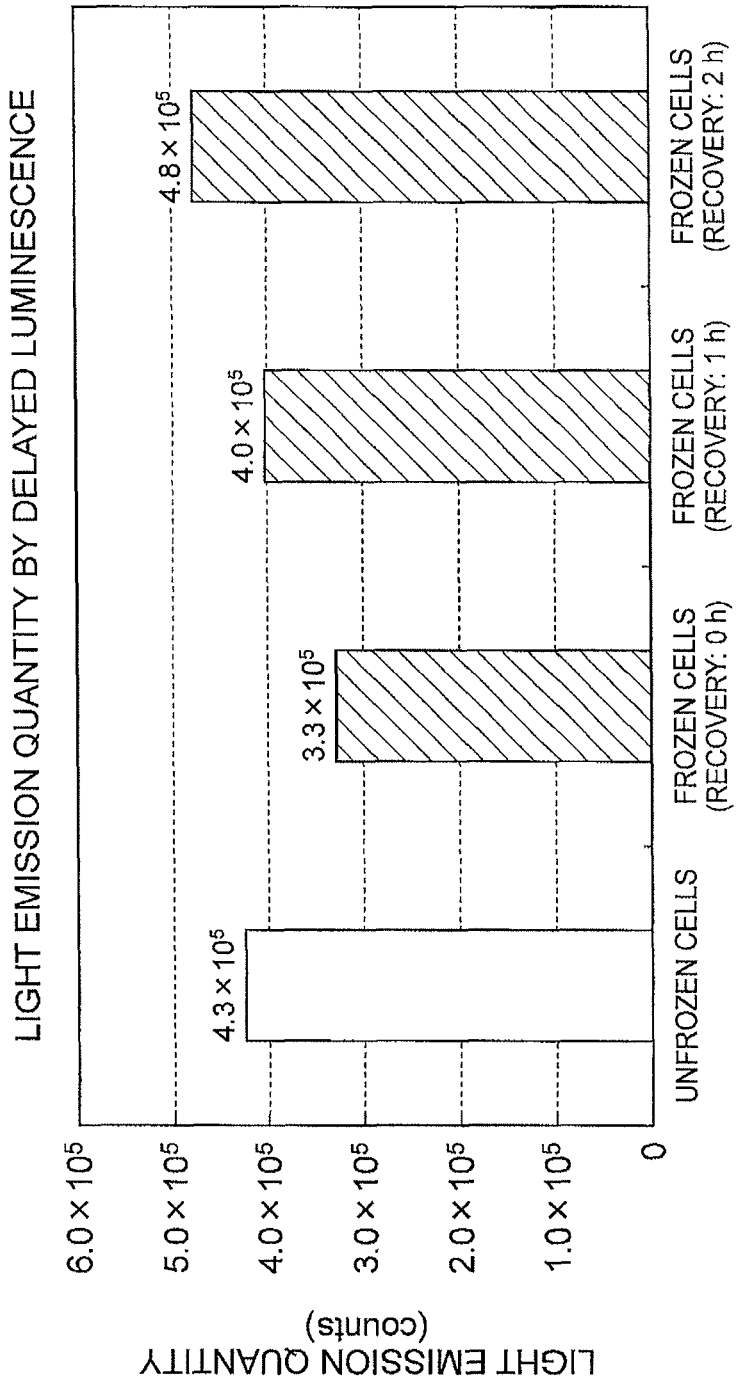
FIG. 24 is a graph representing light emission quantities (integrated values) of the frozen and thawed green algae (Example 5) and unfrozen green algae.
Figure 25:
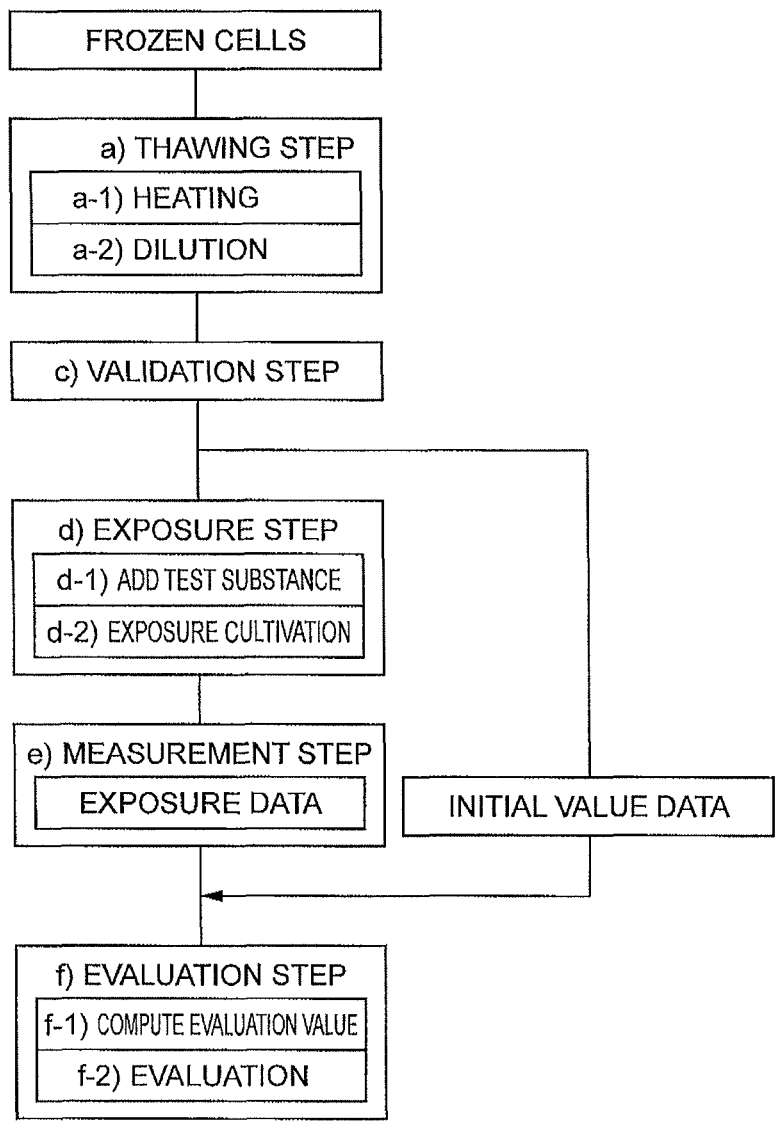
FIG. 25 is a flowchart for illustrating a method of evaluating a toxicity of a chemical substance using the algae in accordance with Comparative Example 2.

FIG. 23 is a graph representing light emission patterns of delayed luminescence. For comparison, it includes the delayed luminescence of the initial value sample obtained by the method of Comparative Example 2 in addition to the delayed luminescence of unfrozen green algae and the delayed luminescence of the initial value sample obtained by the method of the example. As clear from FIG. 23, it is seen that the recovery cultivation for 1 or 2 hr can yield the same light emission pattern as that of the delayed luminescence of unfrozen green algae. FIG. 24 is a graph representing light emission quantities. The recovery cultivation for 1 hr and 2 hr yielded about 93% and 112% of the light emission quantity of unfrozen green algae, respectively, thus attaining sufficient light emission quantities. Hence, the method of the above-mentioned Example 5 can perform an evaluation on a par with the one using unfrozen green algae.

Values in % used in the specification are those rounded off to the nearest integers.

The invention claimed is:

1. A kit for evaluating a toxicity of a chemical substance by delayed luminescence, the kit including a biologically pure strain of cultured algal population and an effective amount of a frost damage protectant,
   wherein said population consists essentially of cultured algal cells frozen in a logarithmic growth phase at −80° C. or less,
   wherein the algal cells are *Pseudokirchneriella subcapitata*,
   wherein the algal population exhibits a bimodal particle size distribution curve, and
   wherein the algal population is brought to a temperature of −80° C. or less in response to human intervention at a point during logarithmic growth phase such that:
       when the algal cells are strain No. NIES-35 in National Institute for Environmental Studies, at least 55% of the total number of the frozen algal cells have a particle size not smaller than that at a valley value in the bimodal particle size distribution curve, or
       when the algal cells are strain ATCC No. 22662 in the American Type Culture Collection, at least 46% of the total number of the frozen algal cells have a particle size not smaller than that at a valley value in the bimodal particle size distribution curve; and
   wherein the kit maintains the frozen algal population at a temperature of −80° C. or less until the algal population is to be thawed in order for a user of the kit to perform the evaluating of the toxicity of a chemical substance.

2. A kit according to claim 1, wherein at least 50% of the total number of the algal cells have a particle size of 4.5 µm or greater.

3. A kit according to claim 1, wherein the algal cells are green algae (*Pseudokirchneriella subcapitata*) preserved as strain No. NIES-35 in National Institute for Environmental Studies; and
   wherein the number of cells at the larger-particle-size peak in the bimodal particle size distribution curve is at least 50% of the total of the number of cells at the smaller-particle-size peak and the number of the cells at the larger-particle-size peak.

4. A kit according to claim 1, wherein the algal cells are green algae (*Pseudokirchneriella subcapitata*) preserved as ATCC No. 22662 in the American Type Culture Collection; and
   wherein the number of cells at the larger-particle-size peak in the bimodal particle size distribution curve is at least 37% of the total of the number of cells at the smaller-particle-size peak and the number of the cells at the larger-particle-size peak.

5. A kit according to claim 1, wherein the algal cells are prepared by a method comprising the steps of:
   cultivating the algal cells in the logarithmic growth phase in a culture solution;
   centrifuging the culture solution containing the algal cells;
   completely removing from the algal cells a culture supernatant separated by the centrifuging; and
   freezing the remaining algal cells at −80° C. or less.

* * * * *